(12) United States Patent
Deisher et al.

(10) Patent No.: US 6,518,236 B1
(45) Date of Patent: *Feb. 11, 2003

(54) FGF HOMOLOGS

(75) Inventors: Theresa A. Deisher, Seattle, WA (US); Darrell C. Conklin, Seattle, WA (US); Fenella Raymond, Seattle, WA (US); Thomas R. Bukowski, Seattle, WA (US); Susan D. Holderman, Seattle, WA (US); Birgit Hansen, Seattle, WA (US); Paul O. Sheppard, Redmond, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/229,947

(22) Filed: Jan. 13, 1999

Related U.S. Application Data

(63) Continuation-in-part of application No. 08/951,822, filed on Oct. 16, 1997, now Pat. No. 5,989,866.
(60) Provisional application No. 60/028,646, filed on Oct. 16, 1996.

(51) Int. Cl.[7] ............ C07K 14/50; A61K 38/18
(52) U.S. Cl. ............. 514/2; 514/12; 530/350; 530/399; 435/69.7
(58) Field of Search .............. 514/2, 12; 530/399, 530/350; 435/69.7

(56) References Cited

U.S. PATENT DOCUMENTS 5,439,818 A   8/1995   Fiddes et al.
5,514,566 A   5/1996   Fiddes et al.
5,604,293 A   2/1997   Fiddes et al.

OTHER PUBLICATIONS

Robson et al. Introduction to Proteins and Protein Engineering. New York, Elsevier, pp. 41, 1986.*

Ngo et al. The Protein Folding Problem and Tertiary Structure. Birkhauser, Boston, pp. 491–495, 1994.*

Wells. Additivity of Mutational Effects in Proteins. Biochemistry. 29(37): 8509–8517, 1990.*

Bowie et al. Deciphering the Message in Protein Sequences: Tolerance to Amino Acid Substitutions. Science 247: 1306–1310, 1990.*

INC313182, LIFESEQ™ Clone Information Results, Incyte Pharmaceuticals Inc., 1995.

Goldfarb, *Cell Growth and Differentiation* 1: 439–445, 1990.

Long et al., *Cell Regulation* 2: 1081–1095, 1991.

Crossley et al., *Cell* 84: 127–136, 1996.

* cited by examiner

*Primary Examiner*—Christine J. Saoud
(74) *Attorney, Agent, or Firm*—Deborah A. Sawislak

(57) ABSTRACT

The present invention relates to polynucleotide and polypeptide molecules for zFGF5 a novel member of the FGF family. The polypeptides, and polynucleotides encoding them, are proliferative for muscle cells, in particular cardiac cells and may be used for remodeling cardiac tissue and improving cardiac function. The present invention also includes antibodies to the zFGF5 polypeptides.

5 Claims, 3 Drawing Sheets

```
FHF-1         ---------MAAAIASSLIRQKRQARESNS-DRVSASKRRSSPSKDG-R 38
FGF-10        ------------------------------------------------
FHF-4         ---------MAAAIASGLIRQKRQAREQHW-DRPSASRRRSSPSKN--R 37
FHF-2         ---------MAAAIASSLIRQKRQARER---EKSNACKCVSSPSKG--K 35
FHF-3         ---------MAALASSLIRQKREVREPGG-SRPVSAQRRVCP-RGT-K 36
FGF4_HUMAN    ---------MS-GPGTAAVALLPAVLLALL-APWAGRGGAAAPTAPN-G 37
FGF6_HUMAN    MALGQKLFITMSRGAGRLQGTLWALVFLGIL-VGMVVP--SPAGTRAN-N 46
FGF2_HUMAN    ------------------------------------------------
FGF1_HUMAN    ------------------------------------------------
KGF-2         ----------MWKWILTHCASAFPHLPGCCC-CCFLLLFLVSSVPVTC-Q 38
FGF7_HUMAN    ----------MHKWILTWILPTLLYR-S-----CFHIICLVGTISLAC-N 33
ZG1_HUZFGF    ----------MY-SAPSACTCLCLHFLLLCF-QVQ-------VLVAEE-N 30
FGF8_HUMAN    ----------MG-SPRSALSCLLLHLLVLCL-QAQEGPGRGPALGREL-A 37
FGF5_HUMAN    ----------MSLSFLLLLFFSHLILSAWAHGEKRLAPKGQPGPAATDRN 40
FGF9_HUMAN    -----------MAPLGEVGNYFGVQDAVPFGNVPVLP--VDSPVLLS-D 35
FGF3_HUMAN    -------------MGLIWLLLLSLLEP-------G-----WPAAGPGA 23

FHF-1         SLCERHV---LGVFSKVRFCSGR----------KRPVRRRPEPQLKGIVT 75
FGF-10        ----------------------------------MASKEPQLKGIVT 13
FHF-4         GLCNGNL---VDIFSKVRIFGLK----------KRRLRRQ-DPQLKGIVT 73
FHF-2         TSCDKNK---LNVFSRVKLFGSK----------KRRRRRP-EPQLKGIVT 71
FHF-3         SLCQKQL---LILLSKVRLCGGRP---------ARPDRGP-EPQLKGIVT 73
FGF4_HUMAN    TLEAELERR-WESLVALSLARLPVAAQPKE-AAVQSGAGDYLLG-IKRLR 84
FGF6_HUMAN    TLLDS--RG-WGTLLSRSRAGL---AG--E-IAGVNWESGYLVG-IKRQR 86
FGF2_HUMAN    ---------MAAGSITTLPALPE---------DGGSGAFPPGHFKDPK 30
FGF1_HUMAN    ---------MAEGEITTFTALTE---------KFN---LPPGNYKKPK 27
KGF-2         ALGQDMVSP-EATNSSSSSFSSPSSAG------RHVRSYNHLQG-DVRWR 80
FGF7_HUMAN    DMTPEQM----ATNVNCS---SPE---------RHTRSYDYMEGGDIRVR 67
ZG1_HUZFGF    VDFRIH-------------VEN-----------QTRARDDVSRKQLRLY 55
FGF8_HUMAN    SLFRAGR---EPQGVSQQHVRE-----------QSLVTDQLSRRLIRTY 72
FGF5_HUMAN    PIGSSSRQSSSSAMSSSSASSSPAASLGSQGSGLEQSSFQWSPS-GRRTG 89
FGF9_HUMAN    HLGQS-------E--AGGLPRGP----------AVTDLDHLKG-ILRRR 64
FGF3_HUMAN    RLRRD--------------AGG-----------RGGVYEHLGG-APRRR 46

FHF-1         RLFSQQ--GYFLQMHPDGTIDGTKDENSDYTLFNLIPVGLR-VVAIQGVK 122
FGF-10        RLFSQQ--GYFLQMHPDGTIDGTKDENSDYTLFNLIPVGLR-VVAIQGVK 60
FHF-4         RLYCRQ--GYYLQMHPDGALDGTKDDSTNSTLFNLIPVGLR-VVAIQGVK 120
FHF-2         KLYSRQ--GYHLQLQADGTIDGTKDEDSTYTLFNLIPVGLR-VVAIQGVQ 118
FHF-3         KLFCRQ--GFYLQANPDGSIQGTPEDTSSFTHFNLIPVGLR-VVTIQSAK 120
FGF4_HUMAN    RLYCNVGIGFHLQALPDGRIGGAHADT-RDSLLELSPVERG-VVSIFGVA 132
FGF6_HUMAN    RLYCNVGIGFHLQVLPDGRISGTHEEN-PYSLLEISTVERG-VVSLFGVR 134
FGF2_HUMAN    RLYCKNG-GFFLRIHPDGRVDGVREKSDPHIKLQLQAEERG-VVSIKGVC 78
FGF1_HUMAN    LLYCSNG-GHFLRILPDGTVDGTRDRSDQHIQLQLSAESVG-EVYIKSTE 75
KGF-2         KLFSFT--KYFLKIEKNGKVSGTKKENCPYSILEITSVEIG-VVAVKAIN 127
FGF7_HUMAN    RLFCRT--QWYLRIDKRGKVKGTQEMKNNYNIMEIRTVAVG-IVAIKGVE 114
ZG1_HUZFGF    QLYSRTS-GKHIQVLG-RRISARGEDGDKYAQLLVETDTFGSQVRIKGKE 103
FGF8_HUMAN    QLYSRTS-GKHVQVLANKRINAMAEDGDPFAKLIVETDTFGSRVRVRGAE 121
FGF5_HUMAN    SLYCRVGIGFHLQIYPDGKVNGSHEAN-MLSVLEIFAVSQG-IVGIRGVF 137
FGF9_HUMAN    QLYCRT--GFHLEIFPNGTIQGTRKDHSRFGILEFISIAVG-LVSIRGVD 111
FGF3_HUMAN    KLYCAT--KYHLQLHPSGRVNGSLENS-AYSILEITAVEVG-IVAIRGLF 92
              *:.        .::          :  .          :  ...   * : .
```

Fig. 1

```
FHF-1       ASLYVAMNGEGYLYSSDV-FTPECKFKESVFENYYVIYSSTLYRQQESG- 170
FGF-10      ASLYVAMNGEGYLYSSDV-FTPECKFKESVFENYYVIYSSTLYRQQESG- 108
FHF-4       TGLYIAMNGEGYLYPSEL-FTPECKFKESVFENYYVIYSSMLYRQQESG- 168
FHF-2       TKLYLAMNSEGYLYTSEL-FTPECKFKESVFENYYVTYSSMIYRQQQSG- 166
FHF-3       LGHYMAMNAEGLLYSSPH-FTAECRFKECVFENYYVLYASALYRQRRSG- 168
FGF4_HUMAN  SRFFVAMSSKGKLYGSPF-FTDECTFKEILLPNNYNAYESYKYPG----- 176
FGF6_HUMAN  SALFVAMNSKGRLYATPS-FQEECKFRETLLPNNYNAYESDLYQG----- 178
FGF2_HUMAN  ANRYLAMKEDGRLLASKC-VTDECFFFERLESNNYNTYRSRKYTS----- 122
FGF1_HUMAN  TGQYLAMDTDGLLYGSQT-PNEECLFLERLEENHYNTYISKKHAEK--N- 121
KGF-2       SNYYLAMNKKGKLYGSKE-FNNDCKLKERIEENGYNTYASFNWQHN--G- 173
FGF7_HUMAN  SEFYLAMNKEGKLYAKKE-CNEDCNFKELILENHYNTYASAKWTHN--G- 160
ZGI_HUZFGF  TEFYLCMNRKGKLVGKPDGTSKECVFIEKVLENNYTALMSAKYSG----- 148
FGF8_HUMAN  TGLYICMNKKGKLIAKSNGKGKDCVFTEIVLENNYTALQNAKYEG----- 166
FGF5_HUMAN  SNKFLAMSKKGKLHASAK-FTDDCKFRERFQENSYNTYASAIHRTEKTG- 185
FGF9_HUMAN  SGLYLGMNEKGELYGSEK-LTQECVFREQFEENWYNTYSSNLYKHVDTG- 159
FGF3_HUMAN  SGRYLAMNKRGRLYASEH-YSAECEFVERIHELGYNTYASRLYRTVSSTP 141
            ::  *.    * *  .      .:*:*.   *         .

FHF-1       ---------RAWFLGLNKEGQIMKG--NRVKKTKPSSHFVPKPIEVCMYR 209
FGF-10      ---------RAWFLGLNKEGQIMKG--NRVEKTKPSSHFVPKPIEVCMYR 147
FHF-4       ---------RAWFLGLNKEGQAMKG--NRVKKTKPAAHFLPKPLEVAMYR 207
FHF-2       ---------RGWYLGLNKEGEIMKG--NHVKKNKPAAHFLPKPLKVAMYK 205
FHF-3       ---------RAWYLGLDKEGQVMKG--NRVKKTKAAAHFLPKLLEVAMYQ 207
FGF4_HUMAN  -----------MFIALSKNGKTKKG--NRVSPTMKVTHFLPRL------- 206
FGF6_HUMAN  -----------TYIALSKYGRVKRG--SKVSPIMTVTHFLPRI------- 208
FGF2_HUMAN  -----------WYVALKRTGQYKLG--SKTGPGQKAILFLPMSAKS---- 155
FGF1_HUMAN  -----------WFVGLKKNGSCKRG--PRTHYGQKAILFLPLPVSSD--- 155
KGF-2       ---------RQMYVALNGKGAPRRG--QKTRRKNTSAHFLPMVVHS---- 208
FGF7_HUMAN  ---------GEMFVALNQKGIPVRG--KKTKKEQKTAHFLPMAIT----- 194
ZGI_HUZFGF  -----------WYVGFTKKGRPRKG--PKTRENQQDVHFMKRYPKGQPEL 185
FGF8_HUMAN  -----------WYMAFTRKGRPRKG--SKTRQHQREVHFMKRLPRGHHTT 203
FGF5_HUMAN  ---------REWYVALNKRGKAKRGCSPRVKPQHISTHFLPRFKQSEQ-P 225
FGF9_HUMAN  ---------RRYYVALNKDGTPREG--TRTKRHQKFTHFLPRPVDPDKVP 198
FGF3_HUMAN  GARRQPSAERLWYVSVNGKGRPRRG--FKTRRTQKSSLFLPRVLDHRDHE 189
            ::..    *    *   :.       *:

FHF-1       EPSLHEIGEKQ----GRS--RKSSGTPTMNGGKVVNQDST---------- 243
FGF-10      EPSLHEIGENK----GVQ--GKFWTPP----------------------- 168
FHF-4       EPSLHDVGETVPKP-GVTPSKSTSASAIMNGGKPVNKSKTT--------- 247
FHF-2       EPSLHDLTEFSRSG-SGTPTKSRSVSGVLNGGKSMSHNEST--------- 245
FHF-3       EPSLHSVPEAS-------P--SSPPAP----------------------- 225
FGF4_HUMAN  --------------------------------------------------
FGF6_HUMAN  --------------------------------------------------
FGF2_HUMAN  --------------------------------------------------
FGF1_HUMAN  --------------------------------------------------
KGF-2       --------------------------------------------------
FGF7_HUMAN  --------------------------------------------------
ZGI_HUZFGF  QKPFKYTTVTK-----RSRR--IRPTHPA--------------------- 207
FGF8_HUMAN  EQSLRFEFLNYPPF-TRSLRGSQRTWAPEPR------------------- 233
FGF5_HUMAN  ELSFTVTVPEKKNP-PSPIKSKIPLSAPRKNTNSVKYRLKFRFG------ 268
FGF9_HUMAN  ELYKDILSQS---------------------------------------- 208
FGF3_HUMAN  MVRQLQSGLPRPPGKGVQPRRRQKQSPDNLEPSHVQASRLGSQLEASAH  239
```

Fig. 2

|    | 1    | 2    | 3    | 4    | 5    | 6    | 7    | 8    | 9    | 10   | 11   | 12   | 13   | 14   | 15   | 16   |
|----|------|------|------|------|------|------|------|------|------|------|------|------|------|------|------|------|
| 1  | 1.00 | 0.39 | 0.43 | 0.29 | 0.46 | 0.33 | 0.36 | 0.38 | 0.37 | 0.41 | 0.39 | 0.40 | 0.42 | 0.40 | 0.35 | 0.38 |
| 2  |      | 1.00 | 0.38 | 0.34 | 0.41 | 0.35 | 0.38 | 0.33 | 0.38 | 0.44 | 0.39 | 0.37 | 0.37 | 0.39 | 0.35 | 0.60 |
| 3  |      |      | 1.00 | 0.31 | 0.42 | 0.34 | 0.33 | 0.36 | 0.34 | 0.38 | 0.35 | 0.37 | 0.41 | 0.46 | 0.35 | 0.35 |
| 4  |      |      |      | 1.00 | 0.34 | 0.53 | 0.26 | 0.24 | 0.26 | 0.31 | 0.28 | 0.30 | 0.30 | 0.31 | 0.28 | 0.32 |
| 5  |      |      |      |      | 1.00 | 0.35 | 0.39 | 0.43 | 0.39 | 0.39 | 0.43 | 0.42 | 0.44 | 0.43 | 0.40 | 0.43 |
| 6  |      |      |      |      |      | 1.00 | 0.33 | 0.31 | 0.33 | 0.31 | 0.32 | 0.34 | 0.34 | 0.32 | 0.36 | 0.36 |
| 7  |      |      |      |      |      |      | 1.00 | 0.34 | 0.98 | 0.33 | 0.76 | 0.81 | 0.34 | 0.37 | 0.67 | 0.42 |
| 8  |      |      |      |      |      |      |      | 1.00 | 0.34 | 0.54 | 0.34 | 0.37 | 0.36 | 0.36 | 0.34 | 0.38 |
| 9  |      |      |      |      |      |      |      |      | 1.00 | 0.33 | 0.66 | 0.72 | 0.34 | 0.37 | 0.62 | 0.42 |
| 10 |      |      |      |      |      |      |      |      |      | 1.00 | 0.32 | 0.35 | 0.40 | 0.37 | 0.32 | 0.43 |
| 11 |      |      |      |      |      |      |      |      |      |      | 1.00 | 0.68 | 0.36 | 0.38 | 0.58 | 0.41 |
| 12 |      |      |      |      |      |      |      |      |      |      |      | 1.00 | 0.36 | 0.33 | 0.62 | 0.42 |
| 13 |      |      |      |      |      |      |      |      |      |      |      |      | 1.00 | 0.47 | 0.34 | 0.32 |
| 14 |      |      |      |      |      |      |      |      |      |      |      |      |      | 1.00 | 0.30 | 0.31 |
| 15 |      |      |      |      |      |      |      |      |      |      |      |      |      |      | 1.00 | 0.38 |
| 16 |      |      |      |      |      |      |      |      |      |      |      |      |      |      |      | 1.00 |

Fig. 3

FGF HOMOLOGS

REFERENCE TO RELATED APPLICATIONS

This application is related to U.S. patent application Ser. No. 08/951,822, filed on Oct. 16, 1997 now U.S. Pat. No. 5,989,866, and Provisional Application 60/028,646, filed on Oct. 16, 1996, for which claims of benefit are made under 35 U.S.C. § 119(e)(1) and 35 U.S.C. § 120.

BACKGROUND OF THE INVENTION

The fibroblast growth factor (FGF) family consists of at least eighteen distinct members (Basilico et al., *Adv. Cancer Res.* 59:115–165, 1992 and Fernig et al., *Prog. Growth Factor Res.* 5(4):353–377, 1994) which generally act as mitogens for a broad spectrum of cell types. For example, basic FGF (also known as FGF-2) is mitogenic in vitro for endothelial cells, vascular smooth muscle cells, fibroblasts, and generally for cells of mesoderm or neuroectoderm origin, including cardiac and skeletal myocytes (Gospodarowicz et al., *J. Cell. Biol.* 70:395–405, 1976; Gospodarowicz et al., *J. Cell. Biol.* 89:568–578, 1981 and Kardami, *J. Mol. Cell. Biochem.* 92:124–134, 1990). In vivo, bFGF has been shown to play a role in avian cardiac development (Sugi et al., *Dev. Biol.* 168:567–574, 1995 and Mima et al., *Proc. Nat'l. Acad. Sci.* 92:467–471, 1995), and to induce coronary collateral development in dogs (Lazarous et al., *Circulation* 94:1074–1082, 1996). In addition, non-mitogenic activities have been demonstrated for various members of the FGF family. Non-proliferative activities associated with acidic and/or basic FGF include: increased endothelial release of tissue plasminogen activator, stimulation of extracellular matrix synthesis, chemotaxis for endothelial cells, induced expression of fetal contractile genes in cardiomyocytes (Parker et al., *J. Clin. Invest.* 85:507–514, 1990), and enhanced pituitary hormonal responsiveness (Baird et al., *J. Cellular Physiol.* 5:101–106, 1987.)

Several members of the FGF family do not have a signal sequence (aFGF, bFGF and possibly FGF-9) and thus would not be expected to be secreted. In addition, several of the FGF family members have the ability to migrate to the cell nucleus (Friesel et al., *FASEB* 9:919–925, 1995). All the members of the FGF family bind heparin based on structural similarities. Structural homology crosses species, suggesting a conservation of their structure/function relationship (Ornitz et al., *J. Biol. Chem.* 271(25):15292–15297, 1996.)

There are four known extracellular FGF receptors (FGFRs), and they are all tyrosine kinases. In general, the FGF family members bind to all of the known FGFRs, however, specific FGFs bind to specific receptors with higher degrees of affinity. Another means for specificity within the FGF family is the spatial and temporal expression of the ligands and their receptors during embryogenesis. Evidence suggests that the FGFs most likely act only in autocrine and/or paracrine manner, due to their heparin binding affinity, which limits their diffusion from the site of release (Flaumenhaft et al., *J. Cell. Biol.* 111(4):1651–1659, 1990.) Basic FGF lacks a signal sequence, and is therefore restricted to paracrine or autocrine modes of action. It has been postulated that basic FGF is stored intracellularly and released upon tissue damage. Basic FGF has been shown to have two receptor binding regions that are distinct from the heparin binding site (Abraham et al.,. *EMBO J.* 5(10):2523–2528, 1986.)

It has been shown that FGFR-3 plays a role in bone growth. Mice made homozygous null for the FGFR-3 (−/−) resulted in postnatal skeletal abnormalities (Colvin et al., *Nature Genet.* 12:309–397, 1996 and Deng et al., *Cell* 84:911–921, 1996). The mutant phenotype suggests that in normal mice, FGFR-3 plays a role in regulation of chrondrocyte cell division in the growth plate region of the bone (Goldfarb, *Cytokine and Growth Factor Rev.* 7(4):311–325, 1996). The ligand for the FGFR-3 in the bone growth plate has not been identified.

Although four FGFRs have been identified, all of which have been shown to have functional splice variants, the possibility that novel FGF receptors exist is quite likely. For example, no receptor has been identified for the FGF-8a isoform (MacArthur et al., *J. Virol.* 69(4):2501–2507, 1995.).

FGF-8 is a member of the FGF family that was originally isolated from mammary carcinoma cells as an androgen-inducible mitogen. It has been mapped to human chromosome 10q25–q26 (White et al., *Genomics* 30:109–11, 1995.) FGF-8 is involved in embryonic limb development (Vogel et al., *Development* 122:1737–1750, 1996 and Tanaka et al., *Current Biology* 5(6):594–597, 1995.) Expression of FGF-8 during embryogenesis in cardiac, urogenital and neural tissue indicates that it may play a role in development of these tissues (Crossley et al., *Development* 121:439–451, 1995.) There is some evidence that acrocephalosyndactylia, a congenital condition marked by peaked head and webbed fingers and toes, is associated with FGF-8 point mutations (White et al., 1995, ibid.)

FGF-8 has five exons, in contrast to the other known FGFs, which have only three exons. The first three exons of FGF-8 correspond to the first exon of the other FGFs (MacArthur et al., *Development* 121:3603–3613, 1995.) The human gene for FGF-8 codes for four isoforms which differ in their N-terminal regions: FGF isoforms a, b, e, and f; in contrast to the murine gene which gives rise to eight FGF-8 isoforms (Crossley et al., 1995, ibid.) Human FGF-8a and FGF-8b have 100% homology to the murine proteins, and FGF-8e and FGF-8f proteins are 98% homologous between human and mouse (Gemel et al., *Genomics* 35:253–257, 1996.)

Heart disease is the major cause of death in the United States, accounting for up to 30% of all deaths. Myocardial infarction (MI) accounts for 750,000 hospital admissions per year in the U.S., with more than 5 million people diagnosed with coronary disease. Risk factors for MI include diabetes mellitus, hypertension, truncal obesity, smoking, high levels of low density lipoprotein in the plasma or genetic predisposition.

Cardiac hyperplasia is an increase in cardiac myocyte proliferation, and has been demonstrated to occur with normal aging in the human and rat (Olivetti et al., *J. Am. Coll. Cardiol.* 24(1):140–9, 1994 and Anversa et al., *Circ. Res.* 67:871–885, 1990), and in catecholamine-induced cardiomyopathy in rats (Deisher et al., *Am. J. Cardiovasc. Pathol.* 5(11):79–88, 1994.) Whether the increase in myocytes originate with some progenitor cell, or are a result of proliferation of a more terminally differentiated cell type, remains controversial.

However, because infarction and other causes of myocardial necrosis appear to be irreparable, it appears that the normal mechanisms of cardiac hyperplasia cannot compensate for extensive myocyte death, and there remains a need for exogenous factors that promote hyperplasia and ultimately result in renewal of the heart's ability to function.

Bone remodeling is the dynamic process by which tissue mass and skeletal architecture are maintained. The process is a balance between bone resorption and bone formation, with two cell types thought to be the major players. These cells are the osteoblast and osteoclast. Osteoblasts synthesize and deposit matrix to become new bone. The activities of osteoblasts and osteoclasts are regulated by many factors, systemic and local, including growth factors.

While the interaction between local and systemic factors has not been completely elucidated, there does appear to be consensus that growth factors play a key role in the regulation of both normal skeletal remodeling and fracture repair.. Some of the growth factors that have been identified in bone include: IGF-I, IGF-II, TGF-$\beta_1$, TGF-$\beta_2$, bFGF, aFGF, PDGF and the family of bone morphogenic proteins (Baylink et al., *J. Bone Mineral Res.* 8 (*Supp.* 2):S565–S572, 1993).

When bone resorption exceeds bone formation, a net loss in bone results, and the propensity for fractures is increased. Decreased bone formation is associated with aging and certain pathological states. In the U.S. alone, there are approximately 1.5 million fractures annually that are attributed to osteoporosis. The impact of these fractures on the quality of the patient's life is immense. Associated costs to the health care system in the U.S. are estimated to be $5–$10 billion annually, excluding long-term care costs.

Other therapeutic applications for growth factors influencing bone remodeling include, for example, the treatment of injuries which require the proliferation of osteoblasts to heal, such as fractures, as well as stimulation of mesenchymal cell proliferation and the synthesis of intramembraneous bone which have been indicated as aspects of fracture repair (Joyce et al. 36th Annual Meeting, Orthopaedic Research Society, Feb. 5–8, 1990. New Orleans, La.).

The present invention provides such polypeptides for these and other uses that should be apparent to those skilled in the art from the teachings herein.

SUMMARY OF THE INVENTION

The present invention provides an isolated polynucleotide molecule encoding a fibroblast growth factor (FGF) homolog comprising a polynucleotide sequence that encodes for a polypeptide that is at least 80% identical to the amino acid sequence as shown in SEQ ID NO: 2 from amino acid residues 55 to 175.

In other embodiments, the polynucleotide molecule encodes for a polypeptide that is at least 80% identical residues 55 to 196 or 207 of SEQ ID NO: 2.

In another aspect, the present invention provides for an isolated polynucleotide molecule comprising a polynucleotide sequence encoding for a polypeptide that is at least 60% identical to the amino acid sequence as shown in SEQ ID NO: 2 from amino acid residues 28 to 175.

In other embodiments, the polynucleotide molecule encodes for a polypeptide that is at least 80% or 90% identical to the amino acid sequence as shown in SEQ ID NO: 2 from amino acid residues 28 to 175.

In another aspect, the present invention provides for an isolated polynucleotide molecule comprising a polynucleotide sequence encoding for a polypeptide that is at least 60% identical to the amino acid sequence as shown in SEQ ID NO: 2 from amino acid residues 28 to 196.

In other embodiments, the polynucleotide molecule encodes for a polypeptide that is at least 80% or 90% identical to the amino acid sequence as shown in SEQ ID NO: 2 from amino acid residues 28 to 196.

In another aspect, the present invention provides for an isolated polynucleotide molecule comprising a polynucleotide sequence encoding for a polypeptide that is at least 60% identical to the amino acid sequence as shown in SEQ ID NO: 2 from amino acid residues 28 to 207.

In other embodiments, the polynucleotide molecule encodes for a polypeptide that is at least 80% or 90% identical to the amino acid sequence as shown in SEQ ID NO: 2 from amino acid residues 28 to 207.

In other aspects, the present invention provides for a polynucleotide molecule as shown in SEQ ID NO: 1 or SEQ ID NO: 6 from nucleotide 163 or 82 to nucleotide 525 or 585.

In other aspects, the present invention provides expression vectors and cultured cells containing DNA segments comprising the polynucleotide molecules encoding for the FGF homolog polypeptides.

In another aspect, the present invention provides for a method of producing an FGF homolog, wherein the cultured cell expresses polypeptide encoded by polynucleotides comprising the sequences disclosed herein.

In another aspect, the present invention provides an isolated FGF homolog polypeptide comprising an amino acid sequence that is at least 80% identical to the sequence as shown in SEQ ID NO: 2 from residues 55 to 175.

In another aspect, the present invention provides for a polypeptide that is at least 60% identical to the sequence of amino acid residues as shown in SEQ ID NO: 2 from residues 28 to 175.

In other embodiments, the polypeptides are at least 80% or 90% identical to the sequence as shown in SEQ ID NO: 2 from residues 28 to 175.

In another aspect, the present invention provides for a polypeptide that is at least 60% identical to the sequence of amino acid residues as shown in SEQ ID NO: 2 from residues 28 to 196.

In other embodiments, the polypeptides are at least 80% or 90i identical to the sequence as shown in SEQ ID NO: 2 from residues 28 to 196.

In another aspect, the present invention provides for a polypeptide that is at least 60% identical to the sequence of amino acid residues as shown in SEQ ID NO: 2 from residues 28 to 207.

In other embodiments, the polypeptides are at least 80% or 90% identical to the sequence as shown in SEQ ID NO: 2 from residues 28 to 207.

In another aspect, the present invention provides for pharmaceutical compositions of the FGF homolog polypeptides in combination with a pharmaceutically acceptable vehicle.

In another aspect, the present invention provides for an FGF homolog fusion protein with a first and second portion joined by a peptide bond.

In another aspect, the present invention provides for a method expanding mesenchymal cells population comprising administering an FGF homolog polypeptide as shown in SEQ ID NO: 2 from residues 28 to 175, wherein the polypeptide increases the number of cells as compared to cell populations without the polypeptide.

In other embodiments, the cells are cardiac myocytes, skeletal myocytes, fibroblasts, osteoblasts and pluripotent stem cells.

In another aspect, the present invention provides for a method for improving cardiac performance in a patient by administering a therapeutic amount of an FGF homolog polypeptide as shown in SEQ ID NO: 2 from residue 28 to residue 175 and results in improvement in cardiac performance.

In other embodiments, the cardiac improvement is measure as increase in total ejection fraction, a decrease in end diastolic pressure, an increase in dP/dt or a decrease in vascular resistance.

In other aspect, the present invention provides for increasing cardiac performance in an individual comprising administering an effective amount of a composition comprising an FGF homolog polypeptide as shown in SEQ ID NO: 2 from residue 28 to residue 175, where the composition results in improved cardiac performance.

BRIEF DESCRIPTION OF THE DRAWINGS

FIG. 1 and FIG. 2 illustrate a multiple alignment of human fibroblast growth factor homologous factor 1 (FHF-1; SEQ ID NO: 21), human myocyte-activating factor (FGF-10; SEQ ID NO: 22), human fibroblast growth factor homologous factor 4 (FHF-4; SEQ ID NO: 23), human fibroblast growth factor homologous factor 2 (FHF-2; SEQ ID NO: 24), human fibroblast growth factor homologous factor 3 (FHF-3; SEQ ID NO: 25), human FGF-4 (SEQ ID NO: 26), human FGF-6 (SEQ ID NO: 27), human FGF-2 (basic; SEQ ID NO: 28), human FGF-1 (acidic; SEQ ID NO: 29), human keratinocyte growth factor 2 (KGF-2; SEQ ID NO: 30), human keratinocyte growth factor precursor (FGF-7; SEQ ID NO: 31), human zFGF5 (SEQ ID NO: 2), human FGF-8 (SEQ ID NO: 32) human FGF-5 (SEQ ID NO: 33), human FGF-9 (SEQ ID NO: 34), and human FGF-3 (SEQ ID NO: 35). "*" designates conserved amino acids; ":" designates conserved amino acid substitutions; and "." designates less stringently conserved amino acid substitutions.

FIG. 3 is an inter-family similarity matrix illustrating the percent identity between: (1) human FGF-5 (SEQ ID NO: 33), (2) human FGF-6 (SEQ ID NO: 27), (3) human FGF-7 (SEQ ID NO: 31), (4) human FGF-8 (SEQ ID NO: 32), (5) human FGF-9 (SEQ ID NO: 34), (6) human zFGF5 (SEQ ID NO: 2), (7) human FGF-10 (SEQ ID NO: 22), (8) human FGF-1 (SEQ ID NO: 29), (9) human FHF-1 (SEQ ID NO: 21), (10) human FGF-2 (SEQ ID NO: 28), (11) human FHF-2 (SEQ ID NO: 24), (12) human FHF-4 (SEQ ID NO: 23), (13) human FGF-3 (SEQ ID NO: 35), (14) human KGF-2 (SEQ ID NO: 30), (15) human FHF-3 (SEQ ID NO: 25), and (16) human FGF-4 (SEQ ID NO: 26).

FIG. 4 is a multiple alignment of the amino acid sequences for mature human zFGFS and mouse zFGF5 (SEQ ID NOS: 2 and 39, respectively).

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952–4, 1985), substance P, Flag™ peptide (Hopp et al., Biotechnology 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of <$10^9$ $M^{-1}$.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGCTTAGCTT-3' are 5'-TAGCTTgagtct-3' and 3'-gtcgacTACCGA-5'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

The term "ortholog" denotes a polypeptide or protein obtained from one species that is the functional counterpart of a polypeptide or protein from a different species. Sequence differences among orthologs are the result of speciation.

A "polynucleotide" is a single- or double-stranded polymer of deoxyribonucleotide or ribonucleotide bases read from the 51 to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA sequence that encodes a fibroblast growth factor (FGF) homolog polypeptide having homology to FGF-8 and FGF-17 (Hoshikawa et al., *Biochem. Biophys. Res. Comm.* 244:187–191, 1998). Analysis of the tissue distribution of the human mRNA corresponding to this novel DNA showed that expression was highest in fetal heart tissue and adult heart tissue, followed by apparent but decreased expression levels in fetal lung, skeletal muscle, smooth muscle tissues such as small intestine, colon and trachea. The FGF homolog polypeptide has been designated zFGF5.

Tissue distribution in murine species does not appear to completely correspond with expression in human tissues. Northern analysis of mouse tissues revealed that expression of mouse zFGF5 is highest in spleen and day 17 embryo, followed by relatively lower expression in heart, lung, kidney and testis. Mouse heart tissue analysis found expression highest in day 16 fetal heart tissue, with expression in adult heart present in most mouse strains. It also appears that there may be variability within murine expression levels and tissues (Hu et al., *Mol. Cell. Biol.* 18:6063–6074, 1998; Ohbayashi et al., *J. Biol. Chem.* 273:18161–18164, 1998 and Maruoka et al., *Mech. Develop.* 74:175–175, 1998).

The novel human zFGF5 polypeptides of the present invention were initially identified by querying an EST database for growth factors. A single EST sequence was discovered and predicted to be related to the FGF family. The novel FGF homolog polypeptide encoded by the full length cDNA contained a motif of the formula: CXFXEX{6}Y, wherein X is any amino acid and X{} is the number of X amino acids greater than one (SEQ ID NO: 36). This motif occurs in all known members of the FGF family and is unique to these proteins.

The nucleotide sequence of the zFGF5 cDNA is described in SEQ ID NO. 1, and its deduced amino acid sequence is described in SEQ ID NO. 2. When amino acid residue 28 (Glu) to amino acid residue 181 (Gln) of SEQ ID NO: 2 is compared to the corresponding region of FGF-8 (See FIGS. 1 and 2) the aligned and deduced amino acid sequence has approximately 560 identity. FGF-17 (Hoshiwara et al., *Biochem. Biophys. Res. Comm.* 244:187–191, 1998) has recently been identified, and has the highest degree of homology to zFGF5. The region of highest identity is ~66% over a 123 amino acid overlap which corresponds to the region of SEQ ID NO: 2 from residue 55 (Tyr) to residue 177 (Arg).

The novel polypeptide encoded by the polynucleotide described herein contains the CXFXE{6}Y motif present in all members of the FGF family. The CXFXE{6}Y motifs (SEQ ID NO: 36) are highly conserved. A consensus amino acid sequence of the CXFXEX{6}Y domain (SEQ ID NO: 36) includes human fibroblast growth factor homologous factor 1 (FHF-1; Smallwood et al., *Proc. Natl. Acad. Sci. USA* 93:9850–9857, 1996), human myocyte-activating factor (FGF-10; HSU76381, GENBANK identifier, http://www.ncbi.nlm.nih.gov/ ), human fibroblast growth factor homologous factor 4 (FHF-4; Smallwood et al., 1996, ibid.), human fibroblast growth factor homologous factor 2 (FHF-2; Smallwood et al., 1996, ibid.), human fibroblast growth factor homologous factor 3 (FHF-3; Smallwood et al., 1996, ibid.), human FGF-4 (Basilico et al., *Adv. Cancer Res.* 59:115–165,1992), human FGF-6 (Basilico et al., 1992, ibid.), human FGF-2 (basic; Basilico et al., 1992, ibid.), human FGF-1 (acidic; Basilico et al., 1992, ibid.), human keratinocyte growth factor 2 (KGF-2; HSU67918 GENBANK identifier, http://www.ncbi.nlm.nih.gov/), human keratinocyte growth factor precursor (FGF-7; Basilico et al., 1992, ibid. ), human zFGF5, human FGF-8 (Gemel et al., *Genomics* 35:253–257, 1996), human FGF-5 (Basilico et al., 1992, ibid.), human FGF-9 (Miyamoto et al., *Mol. Cell. Biol.* 13:4251–4259, 1993), human FGF-3 (Basilico et al., 1992, ibid. ), and FGF-17 (Hoshiwara et al., 1998, ibid.)..

Analysis of the CDNA encoding a zFGF5 polypeptide (SEQ ID NO: 1) revealed an open reading frame encoding 207 amino acids (SEQ ID NO: 2) comprising a mature polypeptide of 180 amino acids (residue 28 to residue 207 of SEQ ID NO: 2). Multiple alignment of ZFGF5 with other known FGFs revealed a block of high percent identity corresponding to amino acid residue 127 (Cys) to amino acid residue 138 (Tyr), of SEQ ID NO: 2 and is shown in FIG. 1. Several of the members of the FGF family do not have signal sequences.

The mouse zFGF5 cDNA was cloned using PCR with a mouse embryo cDNA library as a template and oligonucleotide primers designed from the 5' and 3' ends of the human zFGF5 cDNA. The mouse zFGF5 polynucleotide sequence as shown in SEQ ID NO: 38 and corresponding amino acid sequence as shown in SEQ ID NO: 39 were found to have a high degree of homology. At the amino acid level, the mouse and human polypeptides are approximately 98% identical, with three amino acid changes. The changes as shown in FIG. 4, correspond to a $Val_{26}$ in SEQ ID NO: 2 being $Ala_{26}$ in SEQ ID NO: 39 in the mouse polypeptide, $Pro_{183}$ in SEQ ID NO: 2 to $Ala_{183}$ in SEQ ID NO: 39 and $Ala_{207}$ in SEQ ID NO: 2 to $Gly_{207}$ in SEQ ID NO: 39. As is noted previously, $Ala_{26}$ (mouse) and the corresponding $Val_{26}$ (human) are in the secretory signal sequence, leaving only two amino acid differences in the mature polypeptide. Based on the high identity between the mouse and human sequences, it is predicted that function will be equivalent as well. However, based on differences in tissue distribution for the mouse and human expression, zFGF5 may have a wider organ target distribution, and more diverse biological functions in the mouse than in the human.

Members of the FGF family are characterized by heparin binding domains. A putative heparin-binding domain for zFGF5 has been identified in the region of amino acid residue 148 (Gly) to amino acid residue 169 (Gln) of SEQ ID NO: 2 and SEQ ID NO: 39.

It is postulated that receptor-mediated signaling is initiated upon binding of FGF ligand complexed with cell-surface heparin sulfate proteoglycans. Many FGF family members can be placed into one of two related families on the basis of their structures and functions. aFGF and bFGF consist of three exons separated by two introns of variable length. FGF-8 consists of five exons, the first three of which correspond to the first exon of aFGF and bFGF. All the known FGF family members are spliced to form single polypeptides.

SEQ ID NO: 6 is a degenerate polynucleotide sequence that encompasses all polynucleotides that could encode the zFGF5 polypeptide of SEQ ID NO: 2 (amino acids 1 or 28 to 207). Thus, zFGF5 polypeptide-encoding polynucleotides ranging from nucleotide 1 or 82 to nucleotide 621 of SEQ ID NO: 6 are contemplated by the present invention. Also contemplated by the present invention are fragments and fusions as described above with respect to SEQ ID NO: 1, which are formed from analogous regions of SEQ ID NO: 6, wherein nucleotides 82 to 621 of SEQ ID NO: 6 correspond to nucleotides 82 to 621 of SEQ ID NO: 1, for the encoding a mature zFGFS molecule.

The symbols in SEQ ID NO: 6 are summarized in Table 1 below.

TABLE 1

| Nucleotide | Resolutions | Complement | Resolutions |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |

TABLE 1-continued

| Nucleotide | Resolutions | Complement | Resolutions |
|---|---|---|---|
| K | G\|T | M | A\|C |
| S | C\|G | S | C\|G |
| C\|G | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO: 6, encompassing all possible codons for a given amino acid, are set forth in Table 2 below.

TABLE 2

| Amino Acid | Letter | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B |  | RAY |
| Glu\|Gln | Z |  | SAR |
| Any | X |  | NNN |
| Gap | — | - - - |  |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may have some incorrect amino acids, but one of ordinary skill in the art can easily identify such erroneous sequences by reference to the amino acid sequence of SEQ ID NO: 2.

The highly conserved amino acids in ZFGF5 can be used as a tool to identify new family members. To identify new family members in EST databases, the conserved CXFXEX{6}Y motif (SEQ ID NO: 36) can be used. In another method using polynucleotide probes and hybridization methods, RNA obtained from a variety of tissue sources can be used to generate cDNA libraries and probe these libraries for new family members. In particular, reverse transcription-polymerase chain reaction (RT-PCR) can be used to amplify sequences encoding highly degenerate DNA primers designed from the sequences corresponding to amino acid residue 127 (Cys) to amino acid residue 138 (Tyr) of SEQ ID NO: 2.

Within preferred embodiments of the invention the isolated polynucleotides will serve as a probe and hybridize to similar sized regions of SEQ ID NO: 1 or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is at least about 0.02 M at pH 7 and the temperature is at least about 60° C.

As previously noted, the isolated polynucleotides of the present invention include DNA and RNA. Methods for isolating DNA and RNA are well known in the art. It is generally preferred to isolate RNA from cardiac tissue, although DNA can also be prepared using RNA from other tissues or isolated as genomic DNA. Total RNA can be prepared using guanidine HCl extraction followed by isolation by centrifugation in a CsCl gradient (Chirgwin et al., Biochemistry 18:52–94, 1979). Poly (A)$^+$ RNA is prepared from total RNA using the method of Aviv and Leder (Proc. Natl. Acad. Sci. USA 69:1408–1412, 1972). Complementary DNA (cDNA) is prepared from poly(A)$^+$ RNA using known methods. Polynucleotides encoding zFGF5 polypeptides are then identified and isolated by, for example, hybridization or PCR.

The present invention further provides counterpart polypeptides and polynucleotides from other species (orthologs). Of particular interest are zFGF5 polypeptides from other mammalian species, including murine, rat, porcine, ovine, bovine, canine, feline, equine and other primate proteins. Identification of variants of the human sequence are particularly interesting because while 8 variants of murine FGF-8 have been identifed, only 4 human variants are known. Human variants or orthologs of the human proteins can be cloned using information and compositions provided by the present invention in combination with conventional cloning techniques. For example, a cDNA can be cloned using mRNA obtained from a tissue or cell type that expresses the protein. Suitable sources of mRNA can be identified by probing Northern blots with probes designed from the sequences disclosed herein. A library is then prepared from mRNA of a positive tissue or cell line. A zFGF5-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to zFGF5. Similar techniques can also be applied to the isolation of genomic clones.

Those skilled in the art will recognize that the sequences disclosed in SEQ ID NO: 1 or SEQ ID NO: 38 and SEQ ID NO: 2 and SEQ ID NO: 39 represent a single allele of the human and mouse zFGF5 gene and polypeptide, respectively, and that allelic variation and alternative splicing are expected to occur. Allelic variants can be cloned by probing cDNA or genomic libraries from different individuals according to standard procedures. Allelic variants of the DNA sequence shown in SEQ ID NO: 1 or SEQ ID NO: 38, including those containing silent mutations and those in which mutations result in amino acid sequence changes, are within the scope of the present invention, as are proteins which are allelic variants of SEQ ID NO: 2 or SEQ ID NO: 39.

The present invention also provides isolated zFGF5 polypeptides that are substantially homologous to the polypeptides of SEQ ID NO: 2 and their orthologs. The term "substantially homologous" is used herein to denote polypeptides having 50S, preferably 60%, more preferably at least 80%, sequence identity to the sequences shown in SEQ ID NO: 2 or their orthologs. Such polypeptides will more preferably be at least 90% identical, and most preferably 95% or more identical to SEQ ID NO: 2 or its orthologs. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

preferably of a minor nature, that is conservative amino acid substitutions (see Table 4) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), maltose binding protein (Kellerman and Ferenci, *Methods Enzymol.* 90:459–463, 1982; Guan et al., *Gene* 67:21–30, 1987), or other antigenic epitope or binding domain. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

$$\frac{\text{Total number of identical matches}}{[\text{length of the longer sequence plus the number of gaps introduced into the longer sequence in order to align the two sequences}]} \times 100$$

Sequence identity of polynucleotide molecules is determined by similar methods using a ratio as disclosed above.

Substantially homologous proteins and polypeptides are characterized as having one or more amino acid substitutions, deletions or additions. These changes are

TABLE 4

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |

TABLE 4-continued

Conservative amino acid substitutions

| | |
|---|---|
| Aromatic: | phenylalanine |
| | tryptophan |
| | tyrosine |
| Small: | glycine |
| | alanine |
| | serine |
| | threonine |
| | methionine |

The proteins of the present invention can also comprise, in addition to the 20 standard amino acids, non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxyethyl-cysteine, hydroxyethylhomocysteine, nitroglutamine, homoglutamine, pipecolic acid, tert-leucine, norvaline, 2-azaphenylalanine, 3-azaphenylalanine, 4-azaphenylalanine, 4-fluorophenylalanine, 4-hydroxyproline, 6-N-methyl lysine, 2-aminoisobutyric acid, isovaline and α-methyl serine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations are carried out in a cell free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Meth. Enzymol.* 202:301, 1991; Chung et al., *Science* 259:806–09, 1993; and Chung et al., *Proc. Natl. Acad. Sci. USA* 90:10145–49, 1993). In a second method, translation is carried out in *Xenopus oocytes* by microinjection of mutated mRNA and chemically aminoacylated suppressor tRNAs (Turcatti et al., *J. Biol. Chem.* 271:19991–98, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–76, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

Essential amino acids in the zFGF5 polypeptides of the present invention can be identified according to procedures known in the art, such as site-directed mutagenesis or alanine-scanning mutagenesis (Cunningham and Wells, *Science* 244: 1081–1085, 1989). In the latter technique, single alanine mutations are introduced at every residue in the molecule, and the resultant mutant molecules are tested for biological activity (e.g., receptor binding activity using [125]I-zFGF5 (Moscatelli, *J. Cell Physio.* 131:123–130. 1987), activation of receptor tyrosine kinase (Panek et al.,*J. Pharm. Exp. Therapeutics* 286:569–577, 1998 and Schafer et al., *Anal. Biochem.* 261:100–112, 1998), generation of cardiac myocytes or fibroblasts, or stimulation of bone formation) to identify amino acid residues that are critical to the activity of the molecule. See also, Hilton et al., *J. Biol. Chem.* 271:4699–4708, 1996. Sites of ligand-receptor interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related FGFs and are shown in FIGS. 1 and 2.

Analyses of the amino acid sequence of human and mouse zFGF5 revealed a dibasic site at the C-terminus of the polypeptide (amino acid residue 196–197 (Lys-Arg)). A C-terminally truncated polypeptide comprising an amino acid sequence as shown in SEQ ID NO: 2, from amino acid residue 28 (Glu) to amino acid residue 196 (Lys) was demonstrated to have biological activity. Dibasic amino acids, such as, Arg-X-X-Arg (wherein X is any amino acid residue; SEQ ID NO: 37), Arg-Arg or Lys-Arg; are subject to cleavage by several enzymes, including, but not limited to, thrombin and carboxypeptidases. Therefore, it is within the scope of the claims to make conservative changes at dibasic amino acid residues, in particular the dibasic residues at amino acid residues 196 and 197 (Lys and Arg, respectively) of SEQ ID NO: 2 or SEQ ID NO: 39.

Based on analyses of the FGF family a C-terminally truncated molecule that comprises amino acid residue 28 (Glu) to residue 175 (Met) of SEQ ID NO: 2 may be biologically active. An intramolecular disulfide bond is predicted to occur between amino acid residue 109 (Cys) and residue 127 (Cys) of SEQ ID NO: 2 or SEQ ID NO: 39.

Based on homology alignments with FGF-1 and FGF-2 crystal structures (Eriksson et al., *Prot. Sci.* 2:1274, 1993), secondary structure predictions for beta strand structure of zFGF5 correlates to amino acid residues 56–59, 64–69, 73–76, 85–92, 96–102, 106–111, 115–119, 128–134, 138–144, 149–155, and 173–177 of SEQ ID NO: 2 or SEQ ID NO: 39. Amino acids critical for ZFGF5 binding to receptors can be identified by site-directed mutagenesis of the entire zFGF5 polypeptide. More specifically, they can be identified using site-directed mutagenesis of amino acids in the zFGF5 polypeptide which correspond to amino acid residues in acidic FGF (FGF1) and basic FGF (FGF2) identified as critical for binding of these FGFs to their receptors (Blaber et al., *Biochem.* 35:2086–2094, 1996). These amino acids include Tyr33, Arg53, Asn110, Tyr112, Lys119, Trp123, Leu149 and Met151 in human FGF2, and Tyr30, Arg50, Asn107, Tyr109, Lys116, Trp122, Leu148 and Leu150 in human FGF1, as shown in FIG. 1 and FIG. 2. The corresponding amino acids in zFGF5, as shown in FIG. 1 and FIG. 2, would be Tyr58, Gly77, Asn136, Tyr138, Lys145, Trp149, Met175 and Arg177. One skilled in the art will recognize that other members, in whole or in part, of the FGF family may have structural or biochemical similarities to ZFGF5, and be substituted making such analyses. Such regions would be important for biological functions of the molecule.

An alignment based on homology of zFGF5 with FGF-17 revealed the highest percent identity region consists of a 123 amino acid overlap found between residue 55 (Tyr) and residue 177 (Arg) of SEQ ID NO: 2 with ~66% identity. When conservative amino acid changes are calculated over the same region, the percent homology is ~92%.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Mutagenesis methods as disclosed above can be combined with high-throughput, automated screening methods to detect activity of cloned, mutagenized polypeptides in host cells. Mutagenized DNA molecules that encode active polypeptides (e.g., cell proliferation) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to residues 28 (Glu) to 196 (Lys) or residues 28 (Glu) to 207 (Ala) of SEQ ID NO: 2, allelic variants thereof, or biologically active fragments thereof, and retain the proliferative properties of the wild-type protein. Such polypeptides may also include additional polypeptide segments as generally disclosed above.

The polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al. (eds.), *Current Protocols in Molecular Biology*, John Wiley and Sons, Inc., NY, 1987, which are incorporated herein by reference.

In general, a DNA sequence encoding a zFGF5 polypeptide of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zFGF5 polypeptide into the secretory pathway of a host cell, a secretory signal sequence (also known as a leader sequence, prepro sequence or pre sequence) is provided in the expression vector. The secretory signal sequence may be the native sequence, or a chimera comprising a signal sequence derived from another secreted protein (e.g., t-PA and α-pre-pro secretory leader) or synthesized de novo. The secretory signal sequence is joined to the zFGF5 DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092), and alcohol dehydrogenase genes. See also U.S. Pat. Nos. 4,990,446; 5,063,154; 5,139,936 and 4,661,454. Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et' al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant ($\tau$) of from 1 to 40 milliseconds, most preferably about 20 milliseconds.

Other methods for transforming yeast cells with exogenous DNA and producing recombinant polypeptides therefrom are disclosed by, for example, Kawasaki, U.S. Pat/ No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075, which are incorporated herein by reference. Transformed cells are selected by phenotype determined by the selectable marker, commonly drug resistance or the ability to grow in the absence of a particular nutrient (e.g., leucine). An alternative preferred vector system for use in yeast is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092, which are incorporated herein by reference) and alcohol dehydrogenase genes. See also U.S. Pat. Nos. 4,990,446; 5,063,154; 5,139,936 and 4,661,454, which are incorporated herein by reference. Transformation systems for other yeasts, including *Hansenula polymorpha, Schizosaccharomyces pombe, Kluyveromyces lactis, Kluyveromyces fragilis, Ustilago maydis, Pichia pastoris, Pichia guillermondii,* and *Candida maltosa* are known in the art. A particularly preferred system utilizes *Pichia methanolica (see, PCT application WO 9717450).* For alternative transformation systems, see, for example, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349, which is incorporated herein by reference. Methods for transforming *Acremonium chrysogenum* are disclosed by Sumino et al., U.S. Pat. No. 5,162,228, which is incorporated herein by reference. Methods for transforming Neurospora are disclosed by Lambowitz, U.S. Pat. No. 4,486,533, which is incorporated herein by reference.

Cultured mammalian cells are also preferred hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., eds., *Current Protocols in Molecular Biology,* John Wiley and Sons, Inc., NY, 1987), and liposome-mediated transfection (Hawley-Nelson et al., *Focus* 15:73, 1993; Ciccarone et al., *Focus* 15:80, 1993), which are incorporated herein by reference. The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), BHK 570 (ATCC No. CRL 10314), 293 (ATCC No. CRL 1573; Graham et al., *J. Gen. Virol.* 36:59–72, 1977) and Chinese hamster ovary (e.g. CHO-KL; ATCC No. CCL 61 or DG44) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978, which are incorporated herein by reference) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used.

Other higher eukaryotic cells can also be used as hosts, including insect cells, plant cells and avian cells. Transformation of insect cells and production of foreign polypeptides therein is disclosed by Guarino et al., U.S. Pat. No. 5,162,222; Bang et al., U.S. Pat. No. 4,775,624; and WIPO publication WO 94/06463, which are incorporated herein by reference. The use of *Agrobacterium rhizogenes* as a vector for expressing genes in plant cells has been reviewed by Sinkar et al., *J. Biosci. (Bangalore)* 11:47–58, 1987.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Expressed recombinant zFGF5 polypeptides (or chimeric zFGF5 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can also be isolated by exploitation of their heparin binding properties. For a review, see, Burgess et al., *Ann. Rev. of Biochem.* 58:575–606, 1989. Members of the FGF family can be purified to apparent homogeneity by heparin-Sepharose affinity chromatography (Gospodarowicz et al., *Proc. Natl. Acad. Sci.* 81:6963–6967, 1984) and eluted using linear step gradients of NaCl (Ron et al., *J. Biol. Chem.* 268(4):2984–2988, 1993; *Chromatogralhy: Principles & Methods*, pp. 77–80, Pharmacia LKB Biotechnology, Uppsala, Sweden, 1993; in "Immobilized Affinity Ligand Techniques", Hermanson et al., eds., pp. 165–167, Academic Press, San Diego, 1992; Kjellen et al., *Ann. Rev. Biochem.Ann. Rev. Biochem.* 60:443–474, 1991; and Ke et al., *Protein Expr. Purif.* 3(6):497–507, 1992.)

Other purification methods include using immobilized metal ion adsorption (IMAC) chromatography to purify histidine-rich proteins. Briefly, a gel is first charged with divalent metal ions to form a chelate (E. Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp.529–39). Alternatively, a fusion of the polypeptide of interest and an affinity tag (e.g., polyhistidine, maltose-binding protein, an immunoglobulin domain) may be constructed to facilitate purification.

Protein refolding (and optionally reoxidation) procedures may be advantageously used. It is preferred to purify the protein to >80% purity, more preferably to >90% purity, even more preferably >95%, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

zFGF5 polypeptides or fragments thereof may also be prepared through chemical synthesis. zFGF5 polypeptides may be monomers or multimers; glycosylated or non-glycosylated; pegylated or non-pegylated; and may or may not include an initial methionine amino acid residue.

The activity of molecules of the present invention can be measured using a variety of assays that, for example, measure neogenesis or hyperplasia (i.e., proliferation) of cardiac cells based on the tissue specificity in adult heart. Additional activities likely associated with the polypeptides of the present invention include proliferation of endothelial cells, cardiomyocytes, fibroblasts, skeletal myocytes directly or indirectly through other growth factors; action as a chemotaxic factor for endothelial cells, fibroblasts and/or phagocytic cells; osteogenic factor; and factor for expanding mesenchymal stem cell and precursor populations.

Proliferation can be measured using cultured cardiac cells or in vivo by administering molecules of the claimed invention to the appropriate animal model. Generally, proliferative effects are seen as an increase in cell number and therefore, may include inhibition of apoptosis, as well as mitogenesis. Cultured cells include cardiac fibroblasts, cardiac myocytes, skeletal myocytes, human umbilical endothelial vein cells from primary cultures. Established cell lines include: NIH 3T3 fibroblast (ATCC No. CRL-1658), CHH-1 chum heart cells (ATCC No. CRL-1680), H9c2 rat heart myoblasts (ATCC No. CRL-1446), Shionogi mammary carcinoma cells (Tanaka et al., *Proc. Natl. Acad. Sci.* 89:8928–8932, 1992) and LNCap.FGC adenocarcinoma cells (ATCC No. CRL-1740.) Assays measuring cell proliferation are well known in the art. For example, assays measuring proliferation include such assays as chemosensitivity to neutral red dye (Cavanaugh et al., *Investigational New Drugs* 8:347–354, 1990, incorporated herein by reference), incorporation of radiolabelled nucleotides (Cook et al., *Analytical Biochem.* 179:1–7, 1989, incorporated herein by reference), incorporation of 5-bromo-2'-deoxyuridine (BrdU) in the DNA of proliferating cells (Porstmann et al., *J. Immunol. Methods* 82:169–179, 1985, incorporated herein by reference), and use of tetrazolium salts (Mosmann, *J. Immunol. Methods* 65:55–63, 1983; Alley et al., *Cancer Res.* 48:589–601, 1988; Marshall et al., *Growth Req.* 5:69–84, 1995; and Scudiero et al., *Cancer Res.* 48:4827–4833, 1988; all incorporated herein by reference).

Differentiation is a progressive and dynamic process, beginning with pluripotent stem cells and ending with terminally differentiated cells. Pluripotent stem cells that can regenerate without commitment to a lineage express a set of differentiation markers that are lost when commitment to a cell lineage is made. Progenitor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products and receptors. The stage of a cell population's differentiation is monitored by identification of markers present in the cell population. Myocytes, osteoblasts, adipocytes, chrondrocytes, fibroblasts and reticular cells are believed to originate from a common mesenchymal stem cell (Owen et al., *Ciba Fdn. Symp.* 136:42–46, 1988). Markers for mesenchymal stem cells have not been well identified (Owen et al., *J. of Cell Sci.* 87:731–738, 1987), so identification is usually made at the progenitor and mature cell stages. The existence of early stage cardiac myocyte progenitor cells (often referred to as cardiac myocyte stem cells) has been speculated, but not demonstrated, in adult cardiac tissue. However, recent evidence confirms the presence of myocyte proliferation in end-stage cardiac failure in humans (Kajstura et al., *Proc. Natl. Assoc. Science*, 95:8801–8805, 1998). The novel polypeptides of the present invention are useful to isolate mesenchymal stem cells and cardiac myocyte progenitor cells, both in vivo and ex vivo.

There is evidence to suggest that factors that stimulate specific cell types down a pathway towards terminal differentiation or dedifferentiation, affects the entire cell population originating from a common precursor or stem cell. Thus, the present invention includes stimulating inhibition or proliferation of myocytes, smooth muscle cells, osteoblasts, adipocytes, chrondrocytes and endothelial cells. Molecules of,,the present invention may, while stimulating proliferation or differentiation of cardiac myocytes, inhibit proliferation or differentiation of adipocytes, by virtue of the affect on their common precursor/stem cells. Thus molecules of the present invention, have use in inhibiting chondrosarcomas, atherosclerosis, restenosis, osteoporosis and obesity.

Assays measuring differentiation include, for example, measuring cell-surface markers associated with stage-specific expression of a tissue, enzymatic activity, functional activity or morphological changes (Watt, *FASEB*, 5:281–284, 1991; Francis, *Differentiation* 57:63–75, 1994; Raes, *Adv. Anim. Cell Biol. Technol. Bioprocesses*, 161–171, 1989; all incorporated herein by reference).

In vivo assays for evaluating cardiac neogenesis or hyperplasia include treating neonatal and mature rats with the molecules of the present invention. The animals cardiac function is measured as heart rate, blood pressure, and cardiac output to determine left ventricular function. Post-mortem methods for assessing cardiac improvement include: increased cardiac weight, nuclei/cytoplasmic volume, staining of cardiac histology sections to determine proliferating cell nuclear antigen (PCNA) vs. cytoplasmic actin levels (Quaini et al., *Circulation Res.* 75:1050–1063, 1994 and Reiss et al., *Proc. Natl. Acad. Sci.* 93:8630–8635, 1996.)

In vivo assays for measuring changes in bone formation rates include performing bone histology (see, Recker, R., eds. *Bone Histomorphometry: Techniques and Interpretation.* Boca Raton: CRC Press, Inc., 1983) and quantitative computed tomography (QCT; Ferretti,J. *Bone* 17:353S–364S, 1995; Orphanoludakis et al., *Investig. Radiol.* 14:122–130,, 1979 and Durand et al., *Medical Physics* 19:569–573, 1992). An ex vivo assay for measuring changes in bone formation would be, for example, a calavarial assay (Gowen et al., *J. Immunol.* 136:2478–2482, 1986).

With regard to modulating energy balance, particularly as it relates to adipocyte metabolism, proliferation and differentiation, zFGF5 polypeptides modulate effects on metabolic reactions. Such metabolic reactions include adipogenesis, gluconeogenesis, glycogenolysis, lipogenesis, glucose uptake, protein synthesis, thermogenesis, oxygen utilization and the like. Among other methods known in the art or described herein, mammalian energy balance may be evaluated by monitoring one or more of the aforementioned metabolic functions. These metabolic functions are monitored by techniques (assays or animal models) known to one of ordinary skill in the art, as is more fully set forth below. For example, the glucoregulatory effects of insulin are predominantly exerted in the liver, skeletal muscle and adipose tissue. In skeletal muscle and adipose tissue, insulin acts to stimulate the uptake, storage and utilization of glucose.

Art-recognized methods exist for monitoring all of the metabolic functions recited above. Thus, one of ordinary skill in the art is able to evaluate zFGF5 polypeptides, fragments, fusion proteins, antibodies, agonists and antagonists for metabolic modulating functions. Exemplary modulating techniques are set forth below.

Insulin-stimulated lipogenesis, for example, may be monitored by measuring the incorporation of $^{14}$C-acetate into triglyceride (Mackall et al. *J. Biol. Chem.* 251:6462–6464, 1976) or triglyceride accumulation (Kletzien et al., *Mol. Pharmacol.* 41:393–398, 1992).

zFGF5-stimulated uptake may be evaluated, for example, in an assay for insulin-stimulated glucose transport. Primary adipocytes or NIH 3T3 L1 cells (ATCC No. CCL-92.1) are placed in DMEM containing 1 g/l glucose, 0.5 or 1.0% BSA, 20 mM Hepes, and 2 mM glutamine. After two to five hours of culture, the medium is replaced with fresh, glucose-free DMEM containing 0.5 or 1.0% BSA, 20 mM Hepes, 1 mM pyruvate, and 2 mM glutamine. Appropriate concentrations of zFGF5, insulin or IGF-1, or a dilution series of the test substance, are added, and the cells are incubated for 20–30 minutes. $^3$H or $^{14}$C-labeled deoxyglucose is added to ≈50 $\mu$M final concentration, and the cells are incubated for approximately 10–30 minutes. The cells are then quickly rinsed with cold buffer (e.g. PBS), then lysed with a suitable lysing agent (e.g. 1% SDS or 1 N NaOH). The cell lysate is then evaluated by counting in a scintillation counter. Cell-associated radioactivity is taken as a measure of glucose transport after subtracting non-specific binding as determined by incubating cells in the presence of cytochalasin b, an inhibitor of glucose transport. Other methods include those described by, for example, Manchester et al., *Am. J. Physiol.* 266 (*Endocrinol. Metab.* 29):E326–E333, 1994 (insulin-stimulated glucose transport).

Protein synthesis may be evaluated, for example, by comparing precipitation of $^{35}$S-methionine-labeled proteins following incubation of the test cells with 35S-methionine and $^{35}$S-methionine and a putative modulator of protein synthesis.

Thermogenesis may be evaluated as described by B. Stanley in *The Biology of Neuropeptide Y and Related Peptides*, W. Colmers and C. Wahlestedt (eds.), Humana Press, Ottawa, 1993, pp. 457–509; C. Billington et al., *Am. C. Physiol.* 260:R321, 1991; N. Zarievski et al., *Endocrinology* 133:1753, 1993; C. Billington et al., *Am. J. Physiol.* 266:R1765, 1994; Heller et al., *Am. J. Physiol.* 252(4 Pt 2): R661–7, 1987; and Heller et al., *Am. J. Physiol.* 245(3): R321–8, 1983. Also, metabolic rate, which may be measured by a variety of techniques, is an indirect measurement of thermogenesis.

Oxygen utilization may be evaluated as described by Heller et al., *Pfluaers Arch.* 369(i): 55–9, 1977. This method also involved an analysis of hypothalmic temperature and metabolic heat production. Oxygen utilization and thermoregulation have also been evaluated in humans as described by Haskell et al., *J. Appl. Physiol.* 51 (4): 948–54, 1981.

zFGF5 polypeptides can also be used to prepare antibodies that specifically bind to ZFGF5 epitopes, peptides or polypeptides. Methods for preparing polyclonal and monoclonal antibodies are well known in the art (see, for example, Sambrook et al., *Molecular Cloning; A Laboratory Manual*, Second Edition, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982, which are incorporated herein by reference). As would be evident to one of ordinary skill in the art, polyclonal antibodies can be generated from a variety of warm-blooded animals, such as horses, cows, goats, sheep, dogs, chickens, rabbits, mice, and rats.

The immunogenicity of a zFGF5 polypeptide may be increased through the use of an adjuvant, such as alum (aluminum hydroxide) or Freund's complete or incomplete adjuvant. Polypeptides useful for immunization also include fusion polypeptides, such as fusions of zFGF5 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting only non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Alternative techniques for generating or selecting antibodies useful herein include in vitro exposure of lymphocytes to zFGF5 protein or peptide, and selection of antibody display libraries in phage or similar vectors (for instance, through use of immobilized or labeled zFGF5 protein or peptide).

Antibodies are defined to be specifically binding if they bind to a zFGF5 polypeptide with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art (for example, by Scatchard analysis).

A variety of assays known to those skilled in the art can be utilized to detect antibodies which specifically bind to zFGF5 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant ZFGF5 protein or peptide.

Antibodies to zFGF5 may be used for tagging cells that express zFGF5; to target another protein, small molecule or chemical to heart tissue; for isolating zFGF5 by affinity purification; for diagnostic assays for determining circulating levels of zFGF5 polypeptides; for detecting or quantitating soluble zFGF5 as marker of underlying pathology or disease; in analytical methods employing FACS; for screening expression libraries; for generating anti-idiotypic antibodies; and as neutralizing antibodies or as antagonists to block zFGF5 mediated proliferation in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications.

Molecules of the present invention can be used to identify and isolate receptors involved in cardiac myocyte, cardiac fibroblast, or cardiac progenitor cell proliferation. For example, proteins and peptides of the present invention can be immobilized on a column and membrane preparations run over the column (*Immobilized Affinity Ligand Techniques*, Hermanson et al., eds., Academic Press, San Diego, Calif., 1992, pp.195–202). Proteins and peptides can also be radiolabeled (*Methods in Enzymol.*, vol. 182, "Guide to Protein Purification", M. Deutscher, ed., Acad. Press, San Diego, 1990, 721–737) or photoaffinity labeled (Brunner et al., *Ann. Rev. Biochem.* 62:483–514, 1993 and Fedan et al., *Biochem. Pharmacol.* 33:1167–1180, 1984) and specific cell-surface proteins can be identified.

Antagonists will be useful for inhibiting the proliferative activities of zFGF5 molecules, in cell types such as cardiac cells, including myocytes, fibroblasts and endothelial cells, osteoblasts and chondrocytes. Genes encoding zFGF5 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. : 5,223,409; Ladner et al., U.S. Pat. No. : 4,946,778; Ladner et al., U.S. Pat. No.: 5,403,484 and Ladner et al., U.S. Pat. No. : 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the zFGF5 sequences disclosed herein to identify proteins which bind to zFGF5. These "binding proteins" which interact with zFGF5 polypeptides may be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as zFGF5 "antagonists" to block zFGF5 binding and signal transduction in vitro and in vivo. These anti- zFGF5 binding proteins would be useful for inhibiting expression of genes which result in proliferation or differentiation. Such anti-zFGF5 binding proteins can be used for treatment, for example, in rhabdomyosarcoma, cardiac myxoma, bone cancers of osteoblast origin, and dwarfism, arthritis, ligament and cartilage repair, alone or combination with other therapies.

The molecules of the present invention will be useful for proliferation of cardiac tissue cells, such as cardiac myocytes, myoblasts or progenitors; skeletal myocytes or myoblasts and smooth muscle cells; chondrocytes; endothelial cells; adipocytes and osteoblasts in vitro. For example, molecules of the present invention are useful as components of defined cell culture media, and may be used alone or in combination with other cytokines and hormones to replace serum that is commonly used in cell culture. Molecules of the present invention are particularly useful in specifically promoting the growth and/or development of myocytes in culture, and may also prove useful in the study of cardiac myocyte hyperplasia and regeneration.

The polypeptides, nucleic acid and/or antibodies of the present invention may be used in treatment of disorders associated with heart disease, i.e., myocardial infarction, coronary artery disease, congestive heart failure, hypertrophic cardiomyopathy, myocarditis, congenital heart defects and dilated cardiomyopathy. Molecules of the present invention may also be useful for limiting infarct size following a heart attack, promoting angiogenesis and wound healing following angioplasty or endarterectomy, to develop coronary collateral circulation, for revascularization in the eye, for complications related to poor circulation such as diabetic foot ulcers, for stroke, following coronary reperfusion using pharmacologic methods and other indications where angiogenesis is of benefit. Molecules of the present invention may be useful for improving cardiac function, either by inducing cardiac myocyte neogenesis and/or hyperplasia, by inducing coronary collateral formation, or by inducing remodelling of necrotic myocardial area.

An ischemic event is the disruption of blood flow to an organ, resulting in necrosis or infarct of the non-perfused region. Ischemia-reperfusion is the interruption of blood flow to an organ, such as the heart or brain, and subsequent restoration (often abrupt) of blood flow. While restoration of blood flow is essential to preserve functional tissue, the reperfusion itself is known to be deleterious. In fact, there is evidence that reperfusion of an ischemic area compromises endothelium-dependent vessel relaxation resulting in vasospasms, and in the heart compromised coronary vasodilation, that is not seen in an ischemic event without reperfusion (Cuevas et al., *Growth Factors* 15:29–40, 1997). Both ischemia and reperfusion are important contributors to tissue necrosis, such as a myocardial infarct or stroke. The molecules of the present invention will have therapeutic value to reduce damage to the tissues caused by ischemia or ischemia-reperfusion events, particularly in the heart or brain.

Other therapeutic uses for the present invention include induction of skeletal muscle neogenesis and/or hyperplasia, kidney regeneration and/or for treatment of systemic and pulmonary hypertension.

zFGF5 induced coronary collateral development is measured in rabbits, dogs or pigs using models of chronic coronary occlusion (Landau et al., *Amer. Heart J.* 29:924–931, 1995; Sellke et al., Surgery 120(2):182–188, 1996 and Lazarous et al., 1996, ibid.) zFGF5 benefits for treating stroke is tested in vivo in rats utilizing bilateral carotid artery occlusion and measuring histological changes, as well as maze performance (Gage et al., *Neurobiol. Aging* 9:645–655, 1988). zFGF5 efficacy in hypertension is tested in vivo utilizing spontaneously hypertensive rats (SHR) for systemic hypertension (Marche et al., *Clin. Exp. Pharmacol. Physiol. Suppl.* 1:S114–116, 1995).

Molecules of the present invention can be used to target the delivery of agents or drugs to the heart. For example, the molecules of the present invention will be useful limiting expression to the heart, by virtue of the tissue specific expression directed by the zFGF5 promoter. For example, heart-specific expression can be achieved using a zFGF5-adenoviral discistronic construct (Rothmann et al., *Gene Therapy* 3:919–926, 1996). In addition, the zFGF5 polypeptides can be used to restrict other agents or drugs to heart tissue by linking zFGF5 polypeptides to another protein (Franz et al., *Circ. Res.* 73:629–638, 1993) by linking a first molecule that is comprised of a zFGF5 homolog polypeptide with a second agent or drug to form a chimera. Proteins, for instance antibodies, can be used to form chimeras with zFGF5 molecules of the present invention (Narula et al., *J. Nucl. Cardiol.* 2:26–34, 1995). Examples of agents or drugs include, but are not limited to, bioactive-polypeptides, genes, toxins, radionuclides, small molecule pharmaceuticals and the like. Linking may be direct or indirect (e.g., liposomes), and may occur by recombinant means, chemical linkage, strong non-covalent interaction and the like.

Polynucleotides encoding zFGF5 polypeptides are useful within gene therapy applications where it is desired to increase or inhibit zFGF5 activity. If a mammal has a mutated or absent zFGF5 gene, the zFGF5 gene can be introduced into the cells of the mammal. In one embodiment, a gene encoding a zFGF5 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a zFGF5 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993.

Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types in a tissue with cellular heterogeneity, such as the heart, brain, lungs or liver. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Antisense methodology can be used to inhibit zFGF5 gene transcription, such as to inhibit cell proliferation in vivo. Polynucleotides that are complementary to a segment of a zFGF5-encoding polynucleotide (e.g., a polynucleotide as set froth in SEQ ID NO:1) are designed to bind to zFGF5-encoding mRNA and to inhibit translation of such mRNA. Such antisense polynucleotides are used to inhibit expression of zFGF5 polypeptide-encoding genes in cell culture or in a subject.

The present invention also provides reagents which will find use in diagnostic applications. For example, the zFGF5 gene, a probe comprising zFGF5 DNA or RNA or a subsequence thereof can be used to determine if the zFGF5 gene is present on chromosome 5 and if a mutation in the zFGF5 gene locus has occurred including, but not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; Marian, *Chest* 108:255–65, 1995).

Mice engineered to express the zFGF5 gene, referred to as "transgenic mice," and mice that exhibit a complete absence of zFGF5 gene function, referred to as "knockout mice," may also be generated (Snouwaert et al., *Science* 257:1083, 1992; Lowell et al., *Nature* 366:740–42, 1993; Capecchi, M. R., Science 244: 1288–1292, 1989; Palmiter, R. D. et al. *Annu Rev Genet.* 20: 465–499, 1986). For example, transgenic mice that over-express ZFGF5, either ubiquitously or under a tissue-specific or tissue-restricted promoter can be used to ask whether over-expression causes a phenotype. For example, over-expression of a wild-type zFGF5 polypeptide, polypeptide fragment or a mutant thereof may alter normal cellular processes, resulting in a phenotype that identifies a tissue in which zFGF5 expression is functionally relevant and may indicate a therapeutic target for the zFGF5, its agonists or antagonists. For example, a preferred transgenic mouse to engineer is one that over-expresses the zFGF5 (approximately amino acid residue 28 to residue 207 of SEQ ID NO:2) . Moreover, such over-expression may result in a phenotype that shows similarity with human diseases. Similarly, knockout ZFGF5 mice can be used to determine where zFGF5 is absolutely required in vivo. The phenotype of knockout mice is predictive of the in vivo effects of a zFGF5 antagonist, such as those described herein, may have. These mice may be employed to study the zFGF5 gene and the protein encoded thereby in an in vivo system, and can be used as in vivo models for corresponding human diseases.

In one embodiment of the present invention, a composition comprising ZFGF5 protein is used as a therapeutic agent to enhance osteoblast-mediated bone formation. The compositions and methods using the compositions of the invention may be applied to promote the repair of bone defects and deficiencies, such as those occurring in closed, open and non-union fractures; to promote bone healing in plastic surgery; to stimulate bone ingrowth into non-cemented prosthetic joints and dental implants; in the treatment of periodontal disease and defects; to increase bone formation during distraction osteogenesis; and in treatment of other skeletal disorders that may be treated by stimulation of osteoblastic activity, such as osteoporosis and arthritis. De novo bone formation provided by the methods of the present invention will have use in repair of congenital, trauma-induced, oncologic resection of bone or healing bone following radiation-induced osteonecrosis (Hart et al, *Cancer* 37:2580–2585, 1976). The methods of the present invention may also find use in plastic surgery.

For pharmaceutical use, the proteins of the present invention are formulated for parenteral, particularly intravenous or subcutaneous, administration according to conventional methods. Intravenous administration will be by bolus injection or infusion over a typical period of one to several hours. In general, pharmaceutical formulations will include a zFGF5 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in *Remington's Pharmaceutical Sciences*, Gennaro, ed., Mack Publishing Co., Easton, Pa., 1990, which is incorporated herein by reference. Therapeutic doses will generally be in the range of 0.1 to 100 $\mu$g/kg of patient weight per day, preferably 0.5–20$\mu$ g/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years.

In one embodiment, a therapeutically effective amount of zFGF5 is an amount sufficient to produce a clinically significant change in myocyte proliferation, heart function, bone formation or increases in specific cell types associated with mesenchymal stem cells and progenitors for myocytes, osteoblasts and chondrocytes. In particular, a clinically significant improvement in cardiac performance may be an increase in the number of myocytes or myocyte progenitor cells. Improvements in cardiac performance can be determined by methods well known and accepted by clinicians and those skilled in the art. Such determinations include, but are not limited to, measuring the left ventricular ejection fraction, prior to, and after administration of zFGF5 molecules, and determining at least a 5% increase, preferably 10% or more, in the total ejection fraction, increases in –dP/dt or +dP/dt, greater exercise tolerance, a decrease in vascular resistance, and increased blood flow to the heart. A reduction in symptoms may also be indication of a significant improvement in cardiac performance, and include, for example, reduction in angina pectoris, breathlessness, leg swelling, heart or respiratory rates, edema, fatigue and weakness.

The invention is further illustrated by the following non-limiting examples.

EXAMPLES

Example 1
Extension of EST Sequence

Scanning of a translated DNA database using a query for growth factors resulted in identification of an expressed sequence tag (EST) sequence found to be a novel member of the FGF family, and designated zFGF5.

Oligonucleotide primers ZC11676 (SEQ ID NO: 3) and ZC11677 (SEQ ID NO: 4) were designed from the sequence of an expressed sequence tag (EST). The primers were used for priming internally within the EST, and when PCR was performed using MARATHON READY cDNA (Clontech, Palo Alto, Calif.) from adult heart tissue as template in polymerase chain reaction (PCR).

The conditions used for PCR were 1 cycle at 94° C. for 90 seconds, 35 cycles at 94° C. for 15 seconds; 68° C. for 1 minute; followed by 1 cycle for 10 minutes at 72° C. and 4° C. incubation period. The PCR reaction recreated 160 bp of the EST sequence, and confirmed that EST sequence was correct.

Other libraries that could be amplified with the oligonucleotide primers included skeletal muscle, lung, stomach, small intestine and thyroid.

Example 2
Tissue Distribution

Northerns were performed using Human Multiple Tissue Blots from Clontech (Palo Alto, Calif.). The 160 bp DNA fragment described in Example 1 was electrophoresed on a 1% agarose gel, the fragment was electroeluted, and then radioactively labeled using a random priming MEGAPRIME DNA labeling system (Amersham, Arlington Heights, Ill.) according to the manufacturer's specifications. The probe was purified using a NUCTRAP push column (Stratagene Cloning Systems, La Jolla, Calif.). EXPRESSHYB (Clontech, Palo Alto, Calif.) solution was used for prehybridization and as a hybridrizing solution for the Northern blots. Hybridization took place overnight at 68° C., and the blots were then washed in 2× SSC and 0.05% SDS at RT, followed by a wash in 0.1× SSC and 0.1 SDS at 50° C. A single band was observed at approximately 2.0 kb. Signal intensity was highest for adult heart with relatively less intense signals in skeletal muscle and stomach. Dot blots were probed essentially as described above, confirming that expression for human zFGF5 was highest in heart tissue followed by lung and skeletal muscle.

Example 3
Assay for In Vitro Activity of zFGF5

A.

The mitogenic activity of zFGF5 is assayed using cell lines and cells from a primary culture. Conditioned medium from cells expressing the recombinant protein and/or purified protein is added to cultures of the following cell lines: NIH 3T3 fibroblast (ATCC No. CRL-1658), CHH-1 chum heart cells (ATCC No. CRL-1680), H9c2 rat heart myoblasts (ATCC No. CRL-1446), Shionogi mammary carcinoma cells (Tanaka et al., 1992, ibid.) and LNCaP.FGC adenocarcinoma cells. Freshly isolated cells useful for testing the proliferative activity of zFGF5 include: cardiac fibroblasts, cardiac myocytes, skeletal myocytes and human umbilical vein endothelial cells.

Mitogenic activity is assayed by measurement of $^3$H-thymidine incorporation based on the method of Raines and Ross (*Meth. Enzymolocy* 109:749–773, 1985). Briefly, quiescent cells are plated cells at a density of $3 \times 10^4$ cells/ml in an appropriate medium. A typical growth medium is Dulbecco's Growth Medium (GIBCO-BRL, Gaithersburg, Md.) containing 10% fetal calf serum (FCS). The cells are cultured in 96-well plates and allowed to grow for 3–4 days. The growth medium is removed, and 180 μl of DFC (Table 5) containing 0.1% FCS is added per well. Half the wells have zFGF5 protein added to them and the other half are a negative control, without zFGF5. The cells are incubated for up to 3 days at 37° C. in 5% $CO_2$, and the medium is removed. One hundred microliters of DFC containing 0.1% FCS and 2 μCi/ml $^3$H-thymidine is added to each well, and the plates are incubated an additional 1–24 hours at 37° C. The medium is aspirated off, and 150 μl of trypsin is added to each well. The plates are incubated at 37° C. until the cells detached (at least 10 minutes). The detached cells are harvested onto filters using an LKB Wallac 1295-001 Cell Harvester (LKB Wallac, Pharmacia, Gaithersburg, Md.). The filters are dried by heating in a microwave oven for 10 minutes and counted in an LKB Betaplate 1250 scintillation counter (LKB Wallac) as described by the supplier.

TABLE 5

| | |
|---|---|
| 250 ml | Dulbecco's Modified Eagle's Medium (DMEM, Gibco-BRL) |
| 250 ml | Ham's F12 medium (Gibco-BRL) |
| 0.29 mg/ml | L-glutamine (Sigma, St. Louis, MO) |
| 1 mM | sodium pyruvate (Sigma, St. Louis, MO) |
| 25 mM | Hepes (Sigma, St. Louis, MO) |
| 10 μg/ml | fetuin (Aldrich, Milwaukee, WI) |
| 50 μg/ml | insulin (Gibco-BRL) |
| 3 ng/ml | selenium (Aldrich, Milwaukee, WI) |
| 20 μg/ml | transferrin (JRH, Lenexa, KS) |

B.

Hearts were isolated from 1 day old neonatal mice and then disrupted by repeat collagenase digestions, following the protocol of Brand et al., (*J. Biol. Chem.* 7-268:11500–11503, 1993). Individual myocytes were isolated over a Percoll gradient, and 2 ml were plated in 6 well tissue culture dishes at $0.5 \times 10^6$ cells/ml. Three days later the wells were washed 3 times with PBS without calcium or magnesium, and refed with 1 ml serum free medium (Table 6). The wells were inoculated with $10^{11}$ particles AdCMV-zFGF5 per well or AdCMV-GFP (green fluorescent protein) as a control, and incubated at 37° C. for 8 hours. The wells were then washed again 3 times with PBS without calcium or magnesium, and then refed with 2 mls serum free media.

Within 48 hours after inoculation with the AdCMV-zFGF5, the cultured myocytes have ceased to beat and have undergone a morphologic alteration, while the wells inoculated with the AdCMV-GFP continued to beat spontaneously and are unaffected morphologically by the inoculation. Wells inoculated with AdCMV-zFGF5 also contained, after 48, hours, a confluent layer of viable, non-adherent cells, without any loss in confluence of the adherent myocyte layers, indicating the proliferative activity of the adCMV-zFGF5 on cultured murine myocytes.

TABLE 6

DMEM
Ham's Nutrient Mixture F12 (Gibco-BRL; 1:1 mixture with DMEM)

| | |
|---|---|
| 17 mM | $NaHCO_3$ (Sigma) |
| 2 mM | L-glutamine (Sigma) |
| 1% | PSN (Sigma) |

TABLE 6-continued

DMEM
Ham's Nutrient Mixture F12 (Gibco-BRL; 1:1 mixture with DMEM)

| | |
|---|---|
| 1 µg/ml | insulin |
| 5 µg/ml | transferrin |
| 1 nM | LiCl (Sigma) |
| 1 nM | selenium |
| 25 µg/ml | ascorbic acid (Sigma) |
| 1 nM | thyroxine (Sigma) |

C.

zFGF5 fused to a maltose binding protein (MBP), as described in Example 9A and purified as described in Example 10, was added to myocytes (Example 3B) at a concentration of 0.1 ng/ml. MBP-zFGF5 was shown to stimulate proliferation of myocytes, as well.

Example 4
Assay for Ex Vivo Activity of zFGF5

Cardiac mitogenesis is measured ex vivo by removing entire hearts from neonatal or 8-week old mice or rats. The excised heart is placed in Joklik's (Sigma, St. Louis, Mo.) or Dulbecco's medium at 37° C., 5% $CO_2$ for 4–24 hours. During the incubation period zFGF5 polypeptide is added at a concentration range of 1 pg/ml to 100 µg/ml. Negative controls are using buffer only. $^3$H-thymidine is added and the samples are incubated for 1–4 hours, after which the heart is sectioned and mitogenesis is determined by autoradiography. Sections are used for histomorphometry to determine the nuclei/cytoplasmic volume (McLaughlin, Am. J. Physiol. 271:R122-R129, 1996.)

Alternatively, the heart was lyophilized and resuspended in 1 ml 0.1 N NaOH. The DNA was precipitated using ice cold 10'- trichloroacetic acid (TCA). The supernatant was added to 9 ml scintillation fluid to measure non-specific $^3$H-thymidine incorporation. The resulting pellet was resuspended in 1 ml BTS-450 tissue solubilizer (Beckman, Fullerton, Calif.) and added to 9 ml of scintillation fluid to measure specific DNA incorporation of $^3$H-thymidine.

Left and right ventricles were isolated from 1 day old CD-1 mice (Jackson Labs, Bar Harbor, Me.), and incubated for 4 hours with 3 ng/ml zFGF5Hep2 (n=13; see Example 10) or control (n=10). $^3$H-thymidine was added for 1 hour. The ventricles were washed several times and then homogenized in 1 ml Joklik's medium. The resulting homogenate was added to 9 ml scintillation cocktail and analyzed for total $^3$H-thymidine uptake and DNA incorporation.

zFGF5-Hep2 increased $^3$H-thymidine uptake and incorporation in DNA 2.068±0.489 fold over control, indicating that zFGF5 is mitogenic for a cardiac cell.

Example 5
Assay for In Vivo Activity of zFGF5

The proliferative effects of ZFGF5 are assayed in vivo using two-week old neonatal rats and/or two-month old adult rats. The rats are injected intraperiocardially either acutely or chronically.

A.

Neonatal rats are treated with zFGF5 for 1 to 14 days over a dose range of 50 ng/day to 100 µg/day. After treatment, the effects of zFGF5 versus the sham-treated animals is evaluated by measuring increased cardiac weight, improved in vivo and ex vivo left ventricular function, and by increased cardiac nuclear to cytosolic volume fractions, that are determined histomorphometrically.

B.

Rats with cardiomyopathy induced by chronic catecholamine infusion, by coronary ligation or for models of cardiomyopathy such as the Syrian Cardiomyopathic hamster (Sole et al., Amer. J. Cardiol. 62(11):20G–24G, 1988) are also used to evaluate the effects of zFGF5 on cardiac function and tissue.

To induce cardiomyopathy using catecholamine, 7–8 week old rats are infused continuously with epinephrine for 2 weeks via osmotic minipumps implanted subcutaneously between their shoulder blades. The epinephrine infusion results in an increase in the left ventricular fibrotic lesion score from 0.005±0.005 to 2.11±0.18, scale from 0–3); increased left ventricular myocyte cell width from 17.36±0.46 µm to 23.05±0.62 µm; and negligible left ventricular papillary muscle contractile responses to isoproterenol (0.2 vs 1.1 grams tension compared to saline-infused rats. After the two week treatment period, the rats are injected intraperiocardially daily with either vehicle, zFGF5, bFGF, IGF-I or IGF-II for up to 14 days. The rats are sacrificed and histomorphometry and histocytochemistry are performed.

Rats, treated as described above, are also evaluated at the end of the cathecholamine treatment, and again after growth factor treatment, where cardiac regeneration is measured as decreased left ventricular fibrotic lesion scores, reduced myocyte cell width and increased left ventricular papillary contractile responses to isoproterenol.

Example 6
Chromosomal Mapping of zFGF5

ZFGF5 was mapped to chromosome 5 using the commercially available version of the Whitehead Institute/MIT Center for Genome Research's "GeneBridge 4 Radiation Hybrid Panel" (Research Genetics, Inc., Huntsville, Ala.). The GeneBridge 4 Radiation Hybrid Panel contains DNAs suitable for PCR use from each of 93 radiation hybrid clones, plus two control DNAs (the HFL donor and the A23 recipient). A publicly available wWW server (http://www-genome.wi.mit.edu/cgi-bin/contig/rhmapper.pl) allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of zFGF5 with the "GeneBridge 4 RH Panel", 25 Al reactions were set up in a 96-well microtiter plate (Stratagene, La Jolla, Calif.) and used for PCR in a "RoboCycler Gradient 96" thermal cycler (Stratagene). Each of the 95 PCR reactions consisted of 2.5 µl 50× "Advantage KlenTaq Polymerase Mix" (Clontech), 2 µl dNTPs mix (2.5 mM each; Perkin-Elmer, Foster City, Calif.), 1.25 µl sense primer, ZC11677 (SEQ ID NO; 4) 1.25 µl antisense primer, ZC12053 (SEQ ID NO: 5).

2.5 µl "RediLoad" (Research Genetics, Inc), 0.5 µl "Advantage KlenTaq Polymerase Mix" (Clontech Laboratories, Inc.), 25 ng of DNA from an individual hybrid clone or control and ddH20 for a total volume of 25 µl. The reactions were overlaid with an equal amount of mineral oil and sealed. The PCR cycler conditions were as follows: an initial 1 cycle of 4 minutes at 94° C., 35 cycles of 1 minute at 94° C., 1.5 minute annealing at 66° C. and 1.5 minute extension at 72° C., followed by a final 1 cycle extension of 7 minutes at 72° C. The reactions were separated by electrophoresis on a 36 NuSieve GTG agarose gel (FMC Bioproducts, Rockland, Me.).

The results showed that zFGF5 maps 541.12 cR from the top of the human chromosome 5 linkage group on the WICGR radiation hybrid map. Relative to the centromere, its nearest proximal marker was WI-16922 and its nearest distal marker was WI-14692. The use of surrounding CHLC map markers also helped position zFGF5 in the 5q34–q35 region on the CHLC chromosome 5 version v8c7 integrated marker map (The Cooperative Human Linkage Center, WWW server-Philadelphia, Pa.).

Example 7 zFGF5 Effects on Bone

A.

An adenovirus vector containing the cDNA for zFGF5 was constructed using methods described by Becker et al. (*Methods in Cell Biology* 43:161–189, 1994). Briefly, the cDNA for zFGF5 (as shown in SEQ ID NO: 1) was cloned as a Xba I-Sal I fragment into pACCMV (Gluzman et al., *In Eucaryotic Viral Vectors*, Gluzman (eds.) pp.187–192, Cold Spring Harbor Press, Cold Springs Harbor, N.Y., 1982). The pACCMV vector contains part of the adenovirus 5 genome, the CMV promoter and an SV40 terminator sequence. The plasmid containing the vector and cDNA insert was cotransfected with a plasmid containing the the adenovirus genome, designated pJM17, (McGrory et al., *Virology* 163:614–617, 1988) into 293 cells (ATCC No. CRL-1573; American Type Culture Collection, Canassas, Va.), leading to a recombination event and the production of a recombinant adenovirus containing zFGF5, designated AdCMV-zFGF5. The presence of the zFGF5 CDNA was confirmed by PCR.

The adenovirus vector AdCMV-zFGF5 was used for gene transfer in vivo by intravenous injection of between $1 \times 10^{11}$ and $5 \times 10^{11}$ particles/mouse. It has been shown that after intravenous injection, the majority of the virus targets the liver and very efficiently transduces hepatocytes (Herz et al., *Proc. Natl. Acad. Sci. USA* 90:2812–2816, 1993). It has been demonstrated that the cells produce the protein encoded by the cDNA, and in the case of secreted proteins, secret them into the circulation. High levels of expression and physiological effects have been demonstrated (Ohwada et al., *Blood* 88:768–774, 1996; Stevenson et al., *Arteriosclerosis, Thrombosis and Vascular Biology*, 15:479–484, 1995; Setoguchi et al., *Blood* 84:2946–2953, 1994; and Sakamoto et al., *Proc. Natl. Acad. Sci. USA* 91:12368–12372, 1994).

Six week old CD-1 mice (Jackson Labs, Bar Harbor, Me.) were treated with adenovirus containing no cDNA insert (AdCMV-null) or AdCMV-zFGF5 either IV through the tail vein or intrapericardially (IPC). A total of $5 \times 10^{11}$ viral particles/100 $\mu$l/mouse were given. 14 days after injection, the animals were sacrificed, and tibias and femurs were removed without being separated to examine any potential inflammatory response. The bones were fixed in 10% neutral buffered formalin and processed. They were decalcified in 5% formic acid with 10% sodium citrate, washed in water, dehydrated in a series of 70%–100% ethanol, cleared in xylene and embedded in paraffin. The specimens were cut longitudinally through both tibial and femoral metaphyses and stained with hematoxylin and eosin for identification of bone cells. Osteoblasts were identified by central negative Golgi area and eccentric nucleus, while osteoclasts were identified by multinucleation, non-uniform shape and the Howship's lacunae associated with these resorbing cells.

For bone histomorphometry, femur samples were chosen. Cancellous bone volume was not measured due to variation in the sampling site (i.e., femur samples were not sectioned exactly at the same plane). Three bone parameters were evaluated for histomorphometric changes:

1. Number of endosteal osteoblasts: measured along the endosteal surface of cancellous bone at 180× magnification in an area 1.22 mm proximal to the growth plate.
2. Number of endosteal osteoclasts: measured along the endosteal surface of cancellous bone at 180× magnification in an area 1.22 mm proximal to the growth plate.
3. Growth plate width: measured every 72 $\mu$m at 90× magnification across the entire growth plate except at the peripheral ends to determine the growth plate activity.

Analyses of the data (mean±SD, n=4–7/group) demonstrated the following:

1. There appeared to be no detectable inflammatory response at the joint between tibia and femur.
2. AdCMV-zFGF5 given IV or IPC in mice significantly increased osteogenic activity in the distal femural metaphysis, when examined at 2 weeks. This stimulation of osteogenic activity was indicated by:
    a) significant increases in the number of endosteal osteoblasts in the cancellous bone of distal femurs following IV infusion or IPC injection of AdCMV-zFGF5, 530% and 263%, respectively, when compared with their relative vector only controls; and
    b) the observation of increased osteogenic tissues on the bone surface, suggesting increased differentiation of bone marrow stromal cells toward the osteoblast lineage.
3. The number of endosteal osteoclasts was not significantly affected by IV or IPC administration of AdCMV-zFGF5, when compared with their relative vector only controls.
4. The growth plate width was significantly decreased by IV infusion, but not IPC injection, of AdCMV-zFGF5, suggesting depressed growth plate activity following IV infusion. The differential effects of AdCMV-zFGF5 administrations have not been elucidated.

These results suggest that zFGF5 is a strong mitogen for stimulation of osteoblast proliferation and that zFGF5 has the capacity to induce new bone formation.

B.

Using essentially the same procedures described above in 7.A. QCT was done on female CD-1 (Jackson Labs) that were injected with $1 \times 10^{11}$ particles AdCMV-zFGF5 per mouse. The mice were sacrificed 30 days after injection and heart/tibial length ratios were increased compared to controls (injected with empty adenorvirus or saline). There were no differences between the groups in tibial lengths to account for the change, nor were there differences in any other organ weights among the groups. Thus, the indication is that zFGF5 adenovirus selectively increases total bone density, trabecular bone density, and cortical thickness in the femur, as measured by QCT.

Example 8

Effects of zFGF5 on Heart

As described in 7.B. CD-1 mice were given a single IV injection of AdCMV-zFGF5, sacrificed after four weeks, and the heart/tibial length ratios were found to be increased compared to empty adenovirus or saline treated mice. The results showed that there were no differences between the groups in tibial lengths to account for this change, nor were there differences in any other organ weights among the groups. This result suggests that AdCMV-zFGF5 selectively increased cardiac growth, when administered as an IV adenoviral construct.

Example 9

Expression of zFGF5

A. Construction of zFGF5-Encoding Plasmids zFGF5, a fibroblast growth factor homolog, was expressed in *E. coli* using the MBP (maltose binding protein) fusion system from New England Biolabs (NEB; Beverly, Mass.). In this system, the zFGF5 cDNA was attached to the 3' end of the malE gene to form an MBP-zFGF5 fusion protein. Fusion protein expression was driven by the tac promoter; expression is "off" until the promoter is induced by addition of 1 mmol IPTG (isopropyl b-thiogalactosylpyranoside). Three variations of this fusion protein were made, differing only in their cleavage site for liberating zFGF5 from MBP. One construct had a thrombin cleavage site engineered between the MBP and zFGF5 domains. The second construct had a Factor Xa cleavage site, instead of a thrombin cleavage site. The third construct had an enterokinase cleavage site, instead of the thrombin cleavage site.

The constructs were built as in-frame fusions with MBP in accordance with the Multiple Cloning Site (MCS) of the pMAL-c2 vector (NEB), and according to the manufacturer's specifications. zFGF5 was amplified via PCR using primers which introduced convenient cloning sites, as well as cleavage sites using the following oligonucleotide primers: 1) for the thrombin construct: zc12652 (SEQ ID NO: 7) and zc12631 (SEQ ID NO: 8); 2) for the Factor Xa construct: zc15290 (SEQ ID NO: 9) and zc12631 (SEQ ID NO: 8); and 3) for the enterokinase construct: zc15270 (SEQ ID NO: 10) and zc12631 (SEQ ID NO: 8). In each case, the native zFGF5 signal sequence was not amplified; the zFGF5 as expressed begins at amino acid residue 26 of SEQ ID NO: 2 (Val was changed to an Ala). The thrombin construct was built by inserting an Xba I-Sal I zFGF5 fragment into the Xba I-Sal I sites of pMAL-c2. The Factor Xa construct was built by inserting a blunt-Sal I fragment into the Xmn I-Sal I sites of the MCS. The enterokinase construct was built by inserting an Xba I-Sal I fragment into the Xba-Sal I sites of pMAL-c2. Once the constructs were built, they were transformed into a variety of E. coli host strains and analyzed for high-level expression. The thrombin construct (designated pSDH90.5) was transfected into DH10B cells (GIBCO-BRL), while both the Factor Xa construct (designated pSDH117.3) and the enterokinase construct (designated pSDH116.3) were transfected into TOP10 cells (Invitrogen, San Diego, Calif.). All three MBP fusions are about 63 kD (43 kD in the MBP domain, and approximately 20 kD in the zFGF5 domain).

B. Homologous Recombination/zFGF5

Expression of zFGF5 in Pichia methanolica utilizes the expression system described in co-assigned PCT publication WO97/17450, incorporated herein by reference. An expression plasmid containing all or part of a polynucleotide encoding zFGF5 is constructed via homologous recombination. The expression vector is built from pCZR204, which contains the AUG1 promoter, followed by the αFpp leader sequence, followed by an amino-terminal peptide tag, a blunt-ended SmaI restriction site, a carboxy-terminal peptide tag, a translational STOP codon, followed by the AUG1 terminator, the ADE2 selectable marker, and finally the AUG1 3' untranslated region. Also included in this vector are the URA3 and CEN-ARS sequences required for selection and replication in S. cerevisisiae, and the Amp$^R$ and colE1 ori sequences required for selection and replication in E. coli. The zFGF5 sequence inserted into this vector begins at residue 27 (Ala) of the ZFGF amino acid sequence.

To construct pSDH114, a plasmid for expression of zFGF5 in P. methanolica, the following DNA fragments were introduced into S. cerevisisae: 100 ng of the 'acceptor vector' pCZR204 that has been digested with SmaI; 1 µg of an XbaI-SalI restriction fragment liberated from pSDH90.5 and encompassing zFGF5 coding sequence.; 1 µg of a synthetic, PCR-generated, double-stranded linker segment that spans 70 base pairs of the aFpp coding sequence on one end and joins it to the 70 base pairs of the amino-terminus coding sequence from the mature zFGF5 sequence on the other was generated from the four oligonucleotides zc13497 (SEQ ID NO: 11); zc15131 (SEQ ID NO: 12); zc15132; (SEQ ID NO: 18); zc15134 (SEQ ID NO: 13), of which the sense strand of a double stranded sequence is shown in SEQ ID NO: 19 (5' linker sequence (aFpp→zFGF5 N-terminus)) and 1 µg of of a synthetic, PCR-generated, double-stranded linker segment that spans 70 base pairs of carboxy-terminus coding sequence from zFGF5 on one end with 70 base pairs of AUG1 terminator sequence was generated from the four oligonucleotides 13529 (SEQ ID NO: 14); zc13525 (SEQ ID NO: 15) zc13526 (SEQ ID NO: 16); zc13528 (SEQ ID NO: 17) of which the sense strand of a double stranded sense is shown in the SEQ ID NO: 20 (3' linker sequence (zFGF5 C-terminus→AUG1 terminator)). Ura$^+$ colonies were selected, and DNA from the resulting yeast colonies was extracted and transformed into E. coli. Individual clones harboring the correct expression construct were identified by PCR screening with oligonucleotides zc13497 (SEQ ID NO: 11) and zc13528 (SEQ ID NO: 12) followed by restriction digestion to verify the presence of the zFGF5 insert and DNA sequencing to confirm the desired DNA sequences had been enjoined with one another. Larger scale plasmid DNA is isolated for one of the correct clones, and the DNA is digested with Sfi I to liberate the Pichia-zFGF5 expression cassette from the vector backbone. The Sfi I-cut DNA is then transformed into a Pichia methanolica expression host, designated PMAD16, and plated on ADE D plates for selection. A variety of clones are picked and screened via western blot for high-level zFGF5 expression.

More specifically, for small-scale protein production (e.g., plate or shake flask production), P. methanolica transformants that carry an expression cassette comprising a methanol-regulated promoter (such as the AUG1 promoter) are grown in the presence of methanol and the absence of interfering amounts of other carbon sources (e.g., glucose). For small-scale experiments, including preliminary screening of expression levels, transformants may be grown at 30° C. on solid media containing, for example, 20 g/L Bacto-agar (Difco), 6.7 g/L yeast nitrogen base without amino acids (Difco), 10 g/L methanol, 0.4 mg/L biotin, and 0.56 g/L of -Ade-Thr-Trp powder. Because methanol is a volatile carbon source it is readily lost on prolonged incubation. A continuous supply of methanol can be provided by placing a solution of 50% methanol in water in the lids of inverted plates, whereby the methanol is transferred to the growing cells by evaporative transfer. In general, not more than 1 ml of methanol is used per 100-mm plate. Slightly larger scale experiments can be carried out using cultures grown in shake flasks. In a typical procedure, cells are cultivated for two days on minimal methanol plates as disclosed above at 30° C., then colonies are used to inoculate a small volume of minimal methanol media (6.7 g/L yeast nitrogen base without amino acids, 10 g/L methanol, 0.4 mg/L biotin) at a cell density of about 1×10$^6$ cells/ml. Cells are grown at 30° C. Cells growing on methanol have a high oxygen requirement, necessitating vigorous shaking during cultivation. Methanol is replenished daily (typically $\frac{1}{100}$ volume of 50% methanol per day).

For production scale culturing, fresh cultures of high producer clones are prepared in shake flasks. The resulting cultures are then used to inoculate culture medium in a fermenter. Typically, a 500 ml culture in YEPD grown at 30° C. for 1–2 days with vigorous agitation is used to inoculate a 5-liter fermenter. The cells are grown in a suitable medium containing salts, glucose, biotin, and trace elements at 28° C., pH 5.0, and >30% dissolved O$_2$. After the initial charge of glucose is consumed (as indicated by a decrease in oxygen consumption), a glucose/methanol feed is delivered into the vessel to induce production of the protein of interest. Because large-scale fermentation is carried out under conditions of limiting carbon, the presence of glucose in the feed does not repress the methanol-inducible promoter.

Example 10
Purification of zFGF5

E.coli fermentation medium was obtained from a strain expressing zfGF5 as a Maltose Binding protein fusion (pSDH90.5, as described above). The MBPzFGF5 fusion was solubilized during sonication or French press rupture, using a buffer containing 20 mM Hepes, 0.4 M Nacl, 0.01 M EDTA, 10 mM DTT, at pH 7.4. The extraction buffer also included 5 gg/ml quantities of Pepstatin, Leupeptin, Aprotinin, Bestatin. Phenyl methyl sulfonylfluoride (PMSF) was also included at a final concentration of 0.5 mM.

The extract was spun at 18,000×g for 30 minutes at 4° C. The resulting supernatent was processed on an Amylose resin (Pharmacia LKB Biotechnology, Piscataway, N.J.) which binds the MBP domain of the fusion. Upon washing the column, the bound MBPzFGF5 fusion was eluted in the same buffer as extraction buffer without DTT and protease inhibitors but containing 10 mM Maltose.

The eluted pool of MBPzFGF5 was treated with 1:100 (w/w) Bovine thrombin to MBPzFGF5 fusion. The cleavage reaction was allowed to proceed for 6 to 8 hours at room temperature, after which the reaction mixture was passed over a bed of Benzamidine sepharose (Pharmacia LKB Biotechnology, Piscataway, N.J.) to remove the thrombin, using the same elution buffer as described above for Amylose affinity chromatography.

The passed fraction, containing the cleaved product zFGF5 and free MBP domain were applied to a Toso Haas Heparin affinity matrix (Toso Haas, Montgomeryville, Pa.) equilibrated in 0.5 M NaCl, 20 mM Hepes, 0.01 M EDTA at pH 7.4. The MBP and zFGF5 both bound to heparin under these conditions. The bound proteins were eluted with a 2 to 3 column volume gradient formed between 0.5M NaCl and 2.0 M NaCl in column buffer.

The MBP eluted early, at about 0.7 M NaCl, and the cleaved zFGF5 eluted at about 1.3 M NaCl. The pooled zFGF5 fractions were passed through the amylose step once again to remove any residual MBPzfgf5 that is a minor contaminant. The purified material was designated zFGF5-Hep2, and shows a single highly pure species at ~20 kDa on reducing SDS-PAGE analysis.

Amino acid N-terminal sequencing yielded the native N-Terminal sequence but Mass Spectrophotometry data revealed molecular masses indicating that the C-Terminus must be truncated at residue 196 (Lys) of SEQ ID NO: 2, where a "dibasic site" is present.

zFGF5 protein was very stable in 1.3 M NaCl. Upon dialysis into PBS, the zFGF5 aggregated and left the solution phase. Therefore, formulations that include heparin and other "polyanions" may be used to prevent the aggregation of pure zFGF5.

Example 11
Production of Antibodies

Antibodies for ZFGF5 were produced, using standard techniques known in the art and described previously, by immunizing guinea pigs, rabbits and mice with peptides QTRARDDVSRKQLRLYC (SEQ ID NO: 2 amino acid residue 40 to residue 56), designated zFGF-1; YTTVT-KRSRRIRPTHRAC (SEQ ID NO: 2 amino acid residue 191 to residue 207, with an additional Cys at the C-terminus), designated zFGF5 or the full-length zFGF5 polypeptide as shown in SEQ ID NO: 2, plus the MPB fusion protein, and designated MBP-FGF5. Peptides were conjugated through Cys residues using Maleimide-activated KLH (Pierce Chemical Co., Rockford, Ill.).

Table 7 is a description of the animals, immunization levels and antibody separations.

TABLE 7

| Peptide or Protein | animal | immun. level | Ab produced |
|---|---|---|---|
| ZFGF5-1 | G.P. | 50 ug/animal initial 25 ug/animal boost | Affinity purified and IgG fractionated. |
|  | Rabbit | 100 ug/animal initial 50 ug/animal boost | Affinity purified and IgG fractionated. |
| ZFGF5-2 | G.P. | 50 ug/animal initial 25 ug/animal boost | Affinity purified and IgG fractionated. |
|  | Rabbit | 100 ug/animal initial 50 ug/animal boost | Affinity purified. and IgG fractionated. |
| ZFGF5-MBP | Mouse | 20 ug/animal initial 10 ug/animal boost |  |
|  | Rabbit | 200 ug/animal initial 100 ug/animal boost | Affinity purified |

Example 12
Effects of zFGF5 on ob/ob Mice

The effects of zFGF5 on adipocytes and fat metabolism were examined using female ob/ob mice (C57B1/6J, Jackson Labs, Bar Harbor, Me.). The mice are obese, insulin resistant and have "fatty bone". The mice were weighed and all were found to be the same weight, and were injected IV with $10^{11}$ particles per mouse of AdCMVzFGF5 or either saline or Ad5CMV-GFP for controls, as described in Example 7. 17 days after injection, the control mice injected with Ad5CMV-GFP had gained 5.342±0.5 grams of body weight compared to the day of injection, while the AdCM-VzFGF5 treated mice lost 3.183±0.743 grams of body weight.

Example 13
A. Cloning of Mouse zFGF5

A cDNA for the mouse ortholog of zFGF5 was isolated from a mouse embryo library. Oligonucleotide primers were designed from the full length human zFGF5 sequence (ZC17578 and ZC17579, SEQ ID NOS: 37 and 38, respectively). A PCR reaction was done using 2 µl of library as template and ExTaq polymerase (PanVera, Madison, Wis.) under the following conditions 1 cycle at 94° C. for 15 seconds; 35 cycles at 94° C. for 15 seconds, 60° C. for 20 seconds, 72° C. for 30 seconds; and 1 cycle at 72° C. for 10 minutes. The reaction mixture was incubated a 4° C. overnight. After the first reaction was screened, no positive clones were identified and the procedure was repeated until a positive clone was identified. The positive clones were identified by transforming ElectroMAZ DH10B cells (GibcoBRL) with 1 µl of reaction mixture at 2.3 kV. The cells were plated on culture plates containing ampicillin and methicillin and incubated at room temperature for 3 days.

A DNA fragment obtained by PCR as described above was radiolabeled using a Multiprime DNA Labeling System (Amersham) and used as a probe for filters lifted from culture plates. The filter lifts were hybridized overnight at 65° C. in EXPRESS HYB (Clontech). After hybridiziation, the filters were washed in buffer of 0.25× SSC, 0.25% SDS, 1 mM EDTA at 65° C., 6 times.

Positive clones were identified and cDNA inserts were screened. The clones identified had truncations at the 5' end, complete at the 3' ends and included 3' UTR. One clone, designated LC 7-2 had the longest 5' end when compared to the human zFGF5 sequence. Sequence analysis verified that approximately 52 bp of 5' sequence were missing and that this sequence was in the signal sequence and that the entire nucleotide sequence encoding the mature polypeptide was intact.

B. Northern Analysis

Northern analyses were performed using Mouse Multiple Tissue Blots from Clontech (Palo Alto, Calif.), mouse heart blots (prepared at ZymoGenetics, Inc.) and mouse dot blots (Clontech). Using oligonucleotides ZC17579 (SEQ ID NO: 29) and ZC17578 (SEQ ID NO: 40) and the mouse zFGF5 as a template, a probe was generated. The DNA probe was radioactively labeled using a random priming MEGAPRIME DNA labeling system (Amersham, Arlington Heights, Ill.) according to the manufacturer's specifications. The probe was purified using a NUCTRAP push column (Stratagene Cloning Systems, La Jolla, Calif.). EXPRESSHYB (Clontech, Palo Alto, Calif.) solution was used for prehybridization and as a hybridizing solution for the Northern blots. Hybridization took place overnight at 68° C., and the blots were then washed in 2× SSC and 0.05% SDS at RT, followed by a wash in 0.1× SSC and 0.1% SDS at 50° C. Multiple bands were observed at with predominate bands at approximately 0.6–0.8 kb, 1.2 kb and 2.2–2.4 kb bands depending on the blot used. Signal intensity was highest for spleen with slightly lower intensity signals in heart, lung, liver, skeletal muscle, kidney and testis. Mouse dot blots with the same probe were positive only for spleen and day 17 mouse embryo. Mouse heart mRNA northerns were probed and results were positive for C57 Black, CD1, neonatal heart, and day 16 and day 20 embryo, with strongest signal present in the day 16 embryo. BALB C mouse heart did not have a signal present.

Because the results in the mouse tissue did not directly correlate with results seen in the human tissue, a new probe was designed. The new probe was designed specifically to exclude the possibility that any members of the FGF family other than zFGF5 were positive by Northern analysis. The probe was prepared using PCR with oligonucleotides ZC195687 (SEQ ID NO: 41) and ZC19633 (SEQ ID NO: 42) and template DNA from the mouse cDNA of zFGF5. The reactions were essentially the same as described above. The mouse heart blot was positive for C57 Black mouse, neonatal mouse, days 16 and 20 mouse embryo, with signals strongest in the neonatal heart and day 16 mRNA. The dot blots were positive for spleen and epididymus. It appeared that there was some variability for mouse mRNA expression, unlike human tissue, where heart mRNA consistently was the primarily tissue in which zFGF5 was expressed in humans. Similar variability was seen with rat northern analysis.

Example 14

In vivo Study of Cardiomyopathic Rats

Rats infused subcutaneously with epinephrine for 2 weeks develop a cardiomyopathy quite similar to human idiopathic dilated cardiomyopathy (Deisher et al., *Am. J. Cardiovasc. Pathol.* 5(1):79–88, 1994 and Deisher et al., *J. Pharmacol. Exp. Ther.* 266(1):262–269, 1993.)

The effect of zFGF5 on the initiation and progression of the catecholamine-induced cardiomyopathy was evaluated by administering zFGF5 by intra-pericardial injection to male, Sprague-Dawley rats receiving subcutaneous infusions of epinephrine or saline.

In one protocol, rats (300 gms) were implanted with subcutaneous saline- or epinephrine-filled osmotic mini-pumps under light ether anesthesia. 96 hours following minipump implantation, a single intra-pericardial injection of vehicle (n=25) or zFGF5 at 25, 250 or 500 μg/kg was given (n=10 per dose). Mortality was monitored for an additional two weeks, at the end of which the rats were sacrificed, the hearts were weighed wet, and fixed in 10% neutral buffered formalin for histology.

The zFGF5 had no effect on mortality, body weight, heart weight or cardiac fibrosis in saline-infused rats.

In epinephrine-infused rats, the 25 μg/kg and 250 μg/kg doses reduced mortality from 32% in vehicle injected rats to 0% in 25 μ/kg and 10% in 250 μg/kg injected rats. The highest zFGF5 dose, 500 μg/kg, reduced mortality to 20% compared to vehicle injected rats, however this was not statistically significant. Cardiac fibrosis was determined by scoring Masson's Trichrome stained heart sections. Three sections were scored for each heart, and the average score taken. The fibrosis score for the vehicle-infused hearts was 1.26±0.25, while the score for the 25 μg/kg zFGF5 injection was 1.74±0.23, the 250 μg/kg injection was 1.38±0.29, and the 500 μg/kg injection was 0.81±0.10. The dose of zFGF5 which completely prevented mortality increased the cardiac fibrosis score (25 μg/kg), while the dose which had no effect on mortality reduced the cardiac fibrosis score (500 μg/kg). These results indicate that a pro-fibrotic activity can be beneficial in the setting of heart failure of varying etiologies, of which can include myocardial infarct (MI), idiopathic dilated cardiomyopathy (IDCM), hypertrophic cardiomyopathy, viral myocarditis, congenital abnormalities, and obstructive diseases.

In another protocol, the rats (300 gms) were anesthetized by an intra-muscular injection of an anesthetic cocktail ketamine:rompun:acepromazine (1:1:0.1). Subcutaneous epinephrine-filled osmotic mini-pumps were implanted, and either vehicle or zFGF5 was injected intra-pericardially immediately afterward at 25 μg/kg (n=25 per group). For the vehicle injected rats, 21% had died within 6 days following the epinephrine-filled minipump implantation, while none of the zFGF5 injected rats had died. By the end of the 2 week epinephrine infusion period, 25–6 of the vehicle-injected rats had died, while only 226 of the zFGF5-injected rats had died. In this model, zFGF5 co-treatment at the time of minipump implantation delayed mortality by at least 7 days.

Example 15

Mammalian Expression Constructs

An expression plasmid containing all or part of a polynucleotide encoding zFGF5 is constructed via homologous recombination. A fragment of zFGF5 cDNA is isolated using PCR that includes the polynucleotide sequence from nucleotide 1 to nucleotide 621 of SEQ ID NO: 1 or SEQ ID NO: 37, with flanking regions at the 5' and 3' ends corresponding to the vectors sequences flanking the zFGF5 insertion point. The primers for PCR each include from 5' to 3' end: 40 bp of flanking sequence from the vector and 17 bp corresponding to the amino and carboxyl termini from the open reading frame of zFGF5.

Ten µl of the 100 µl PCR reaction is run on a 0.86 LMP agarose gel (Seaplaque GTG) with 1×TBE buffer for analysis. The remaining 90 µl of PCR reaction is precipitated with the addition of 5 µl 1 M NaCl and 250 µl of absolute ethanol. The plasmid pZMP6 which has been cut with SmaI is used for recombination with the PCR fragment.

Plasmid pZMP6 was constructed from pZP9 (deposited at the American Type Culture Collection, 10801 University Boulevard, Manassas, Va. 20110–2209, and is designated No. 98668) with the yeast genetic elements taken from pRS316 (deposited at the American Type Culture Collection, 10801 University Boulevard, Manassas, Va. 20110–2209, and designated No. 77145), an IRES element from poliovirus, and the extracellular domain of CD8, truncated at the carboxyl terminal end of the transmembrane domain. pZMP6 is a mammalian expression vector containing an expression cassette having the cytomegalovirus immediate early promoter, immunoglobulin signal peptide intron, multiple restriction sites for insertion of coding sequences, a stop codon and a human growth hormone terminator. The plasmid also has an E. coli origin of replication, a mammalian selectable marker expression unit having an SV40 promoter, enhancer and origin of replication, a DHFR gene, the SV40 terminator, as well as the URA3 and CEN-ARS sequences required for selection and replication in S. cerevisiae.

One hundred microliters of competent yeast cells (S. cerevisiae) are independently combined with 10 µl of the various DNA mixtures from above and transferred to a 0.2 cm electroporation cuvette. The yeast/DNA mixtures are electropulsed at 0.75 kv (5 kV/cm), ∞ ohms, 25 µF. To each cuvette is added 600 µl of 1.2 M sorbitol and the yeast is plated in two 300 µl aliquots onto two URA-D plates and incubated at 30° C. After about 48 hours, the Ura+ yeast transformants from a single plate are resuspended in 1 ml $H_2O$ and spun briefly to pellet the yeast cells. The cell pellet is resuspended in 1 ml of lysis buffer (2F Triton X-100, 1k SDS, 100 mM NaCl, 10 mM Tris, pH 8.0, 1 mM EDTA). Five hundred microliters of the lysis mixture is added to an Eppendorf tube containing 300 µl acid washed glass beads and 200 µl phenol-chloroform, vortexed for 1 minute intervals two or three times, followed by a 5 minute spin in a Eppendorf centrifuge at maximum speed. Three hundred microliters of the aqueous phase is transferred to a fresh tube, and the DNA precipitated with 600 µl ethanol (EtOH), followed by centrifugation for 10 minutes at 4° C. The DNA pellet is resuspended in 10 µl $H_2O$.

Transformation of electrocompetent E. coli cells (DH10B, GibcoBRL) is done with 0.5–2 ml yeast DNA prep and 40 ul of DH10B cells. The cells are electropulsed at 1.7 kV, 25 µF and 400 ohms. Following electroporation, 1 ml SOC (26 Bacto Tryptone (Difco, Detroit, Mich.), 0.5% yeast extract (Difco), 10 mM NaCl, 2.5 mM KCl, 10 mM MgCl2, 10 mM MgSO4, 20 mM glucose) is plated in 250 µl aliquots on four LB AMP plates (LB broth (Lennox), 1.8% Bacto Agar (Difco), 100 mg/L Ampicillin).

Individual clones harboring the correct expression construct for zFGF5 are identified by restriction digest to verify the presence of the zFGF5 insert and to confirm that the various DNA sequences have been joined correctly to one another. The insert of positive clones are subjected to sequence analysis. Larger scale plasmid DNA is isolated using the Qiagen Maxi kit (Qiagen) according to manufacturer's instruction.

Example 16

Mammalian Expression of zFGF5

CHO DG44 (Chasin et al., Som. Cell. Molec. Genet. 12:555–666, 1986) are plated in 10 cm tissue culture dishes and allowed to grow to approximately 50 to 70% confluency overnight at 37° C., 5% $CO_2$, in Ham's F12/FBS media (Ham's F12 medium, (Gibco BRL, Gaithersburg, Md.), 5% fetal bovine serum (Hyclone, Logan, Utah), 1% L-glutamine (JRH Biosciences, Lenexa, Kans.), 1% sodium pyruvate (Gibco BRL)). The cells are then transfected with the plasmid zFGF5/pZMP6, using Lipofectamine™ (Gibco BRL), in serum free (SF) media formulation (Ham's F12, 10 mg/ml transferrin, 5 mg/ml insulin, 2 mg/ml fetuin, 1% L-glutamine and 1% sodium pyruvate). ZFGF5/pZMP6 is diluted into 15 ml tubes to a total final volume of 640 µl with SF media. 35 µl of Lipofectamine™ (Gibco BRL) is mixed with 605 µl of SF medium. The Lipofectamine™ mix is added to the DNA mix and allowed to incubate approximately 30 minutes at room temperature. Five milliliters of SF media is added to the DNA:Lipofectamine™ mixture. The cells are rinsed once with 5 ml of SF media, aspirated, and the DNA:Lipofectamine™ mixture is added. The cells are incubated at 37° C. for five hours, then 6.4 ml of Ham's F12/10% FBS, 11 PSN media is added to each plate. The plates are incubated at 37° C. overnight and the DNA:Lipofectamine™ mixture is replaced with fresh 5% FBS/Ham's media the next day. On day 3 post-transfection, the cells are split into T-175 flasks in growth medium. On day 7 postransfection the cells are stained with FITC-anti-CD8 monoclonal antibody (Pharmingen, San Diego) followed by anti-FITC-conjugated magnetic beads (Miltenyi Biotec, Auburn, Calif.). The CD8 positive cells are separated by Miltenyi mini-MACS columns according to manufacturer's directions (Miltenyi Biotec), and put into DMEM/Ham's F12/5% FBS without nucleosides but with 50 nM methotrexate (selection medium).

Cells are plated for subcloning at a density of 0.5, 1 and 5 cells per well in 96 well dishes in selection medium and allowed to grow out for approximately two weeks. The wells are checked for evaporation of medium and brought back to 200 µl per well as necessary during this process. When a large percentage of the colonies in the plate are near confluency, 100 µl of medium is collected from each well for analysis by dot blot, and the cells are fed with fresh selection medium. The supernatant is applied to a nitrocellulose filter in a dot blot apparatus, and the filter is treated at 100° C. in a vacuum oven to denature the protein. The filter is incubated in 625 mM tris glycine, pH 9.1, 5 mM βmercaptoethanol, at 65° C., 10 minutes, then in 2.5% non-fat dry milk Western A Buffer (0.25% gelatin, 50 mM TrisHCl pH 7.4, 150 mM NaCl, 5 mM EDTA, 0.05% Igepal, Sigma) overnight at 4° C. on a rotating shaker. The filter is incubated with the antibody-HRP conjugate in 2.5% non-fat dry milk Western A buffer for 1 hour at room temperature on a rotating shaker. The filter is washed three times at room temperature in PBS plus 0.01% Tween 20, 15 minutes per wash. The filter was developed with ECL reagent according to manufacturer's directions (Amersham, Arlington Heights, Ill.), and exposed to film (Hyperfilm ECL, Amersham) approximately 5 minutes. Positive clones are trypsinized from the 96 well dish and transferred to 6 well dishes in selection medium for scaleup and analysis by Western blot.

Example 17

Expansion of Cells From Bone Marrow

Assays were performed to measure the frequency of fibroblast colony forming units from monkey low density, non-adherent cells isolated from bone marrow. This assay is indicative of mesenchymal stem cell frequency.

One half of a 96 well microtiter plate is inoculated with cells at a density of 10,000 cells/well and the other half of the plate is inoculated with cells at a density of 1,000 cells/well. The culture medium is a MEM (GIBCO-BRL, Gaithersburg, Md.), 2% bovine serum albumin, 10 µg/ml insulin, 200 µg/ml transferrin, antibiotic and 50 µM β-Mercaptoethanol. The cells are incubated at 37° C. in 5% $CO_2$ for 14 days and then stained with toluidine blue to improve cell visibility and examined microscopically. Positive wells have at least 50 cells exhibiting a "stromal" morphology, i.e., large, spread out cells. The positive control is medium containing 20% fetal bovine serum. Results demonstrated that zFGF5, at a concentration of 100 ng/ml increased the frequency of CFU-F to levels equivalent to the positive control of 20% FBS.

Example 18

Neurite Outgrowth Assay

The effect of zFGF5 on PC12, rat pheochromocytoma cells with neural potential (ATCC No. CRL-1721, American Type Culture Collection, 10801 University Boulevard, Manassas, Va. 20110–2209) examined using the following growth factors, each at 3 dilutions:

1 µg/ml, 100 ng/ml, and 10 ng/ml neural growth factor (NGF; source and location) in medium containing RPMI 1640 (R&D Systems, Minneapolis, Minn.)

1 µg/ml, 100 ng/ml, and 10 ng/ml human basic FGF (R&D Systems, Minneapolis, Minn.)

1 µg/ml, 100 ng/ml, and 10 ng/ml zFGF5 (recombinantly produced in E. coli.)

1 µg/ml, 100 ng/ml, and 10 ng/ml zFGF5 (recombinantly produced in CHO cells)

The PC12 cells were plated at a concentration of $5 \times 10^4$/ml onto collagen coated 24 well culture plates and incubated for 48 hours in the appropriate medium. After 48 hours, the medium was changed to include one of the cytokines described above and then changed again every 2 days. The wells were scored for relative neurite outgrowth on days 6 and 9.

Neurite outgrowth was induced with each of the cytokines. NGF and bFGF appeared to have similar affinity, while zFGF5 had significantly lower affinity. NGF exerted the greatest extent of neural outgrowth activity, followed by bFGF, with significantly lower activity seen with zFGF5.

Example 19

Identification of a Target Cell

Identification of a putative mesenchymal stem cell as a target for zFGF5 was made using FITC-labeled protein and neonatal mouse heart tissue.

ZFGF5, purified as described above, was dialyzed into 0.1 M sodium bicarbonate pH 9.0. Fluorescein isothiocyanate (FITC; Molecular Probes, Eugene, Ore.) was dissolved at 1 mg/ml in the same buffer without exposure to strong light. The mixture was prepared containing 1 mg FITC/1 mg zFGF5, and reacted for 1–2 hours in the dark at room temperature. The reaction was stopped by adding 1 M glycine to a final concentration of 0.1 M, then reacted for 1 hour at room temperature. The mixture was then dialyzed against 0.1 M sodium biocarbonate to make a 1:500–1:1000 dilution for 3 hours. The dialysis solution was changed and the process repeated for 3–18 hours to remove unlabeled FITC.

Neonatal mouse heart ventricles were isolated, minced, and repeatedly washed in phosphate buffered solution (PBS) until all red blood cells and debris were removed. The minced ventricles were placed in a solution containing 18 ml PBS and 1k glucose and 1 ml of 2% DNAse/Collagenase solution was added. The mixture was incubated on a shaker for 30 minutes at 37° C. The supernatant was discarded and the process was repeated once more. After incubation, the supernatant (~20 ml) was transferred to a tube containing 20 ml DF 20 (Dulbecco's Modified Eagle's Medium/Ham's Nutrient Mixture F12, 1:1 (GIBCO-BRL, Gaithersburg, Md.) and 20% fetal bovine serum). After mixing, the tubes were centrifuged at 1650 rpms in a Beckman CS-6R centrifuge (Beckman, Fullerton, Calif.) at 4° C. for 10 minutes. The supernatant was discarded and the pellet was resuspended in DF 10 (10% FBS). The cells were kept cold and spun again and resuspended in 40 ml of DF 10. The cell mixture was passed over a 40 µm filter (Becton Dickinson, Detroit, Mich.) and counted using a hemacytometer.

The cells were incubated in FITC-labeled zFGF5 at 4° C. for 30 minutes at a concentration of $2 \times 10^6$ cells/1 µg zFGF5. After incubation, the cells were spun at 1650 rpms in a Beckman CS-6R centrifuge (Beckman) for 5 minutes. The supernatant was discarded and the pellet washed once in 10 ml of DF 10 and resuspended in 4 ml DF 10.

10 µl of MACS anti-FITC microbeads (Miltenyi Biotech, Auburn, Calif.) were mixed with $10^7$ cells in 4 ml of DF10 and incubated at 4° C. for 30 minutes.

MACS positive selection type LS+ separation columns (Miltenyi Biotech) were washed with 3 ml of MAC buffer (PBS, 0.50% BSA, 2 mM EDTA) and the cell/bead mixture was washed in 10 ml MAC buffer and then resuspended in 6 ml MAC buffer. The cell/bead mixture was divided between the two columns and the first negative fraction was discarded. 1.5 ml of 0.6 M NaCl was added to each column and eluted but not collected. The columns were then washed with 1.5 ml MAC buffer. The cells bound with FITC-labeled zFGF5 were collected by adding 3 ml MAC buffer, removing the column from the magnet and flushing out the positive cells using the plunger. The positive cell fraction was plated in a T75 flask and 50 ml of plating medium was added (DF with 15% FBS and antibiotics). The cells were incubated at 37° C. for 1 week and counted. The yield of positive cells was approximately 0.1% of original total cells counted.

Cells binding FITC-labeled zFGF5 were examined by transmission electronmicroscopy (TEM). The cells were between 3–5 microns in diameter. The cell nuclei occupied the majority of the cell volume, and few cytoplasmic organelles were apparent. The phenotype identified by TEM identifies the zFGF5-isolated cells as primitive mesenchymal stem cells.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated FGF homolog polypeptide comprising an amino acid sequence as shown in SEQ ID NO: 2 from amino acid residue 55 (Tyr) to amino acid residue 175 (Met).

2. The polypeptide of claim 1, wherein said polypeptide comprises the amino acid sequence as shown in SEQ ID NO: 2 from amino acid residue 28 (Glu) to amino acid residue 175 (Met).

3. A pharmaceutical composition comprising a purified FGF homolog polypeptide according to claim 1, in combination with a pharmaceutically acceptable vehicle.

4. A fusion protein comprising a first portion and a second portion, joined by a peptide bond, said first portion comprises a maltose binding protein, and said second portion comprises an FGF homolog polypeptide comprising amino acid residues 28–207 of SEQ ID NO: 2.

5. The fusion protein of claim 4, wherein the peptide bond is selected from the group consisting of Factor Xa cleavage site, thrombin cleavage site and enterokinase cleavage site.

* * * * *

SEQUENCE LISTING

<160> NUMBER OF SEQ ID NOS: 43

<210> SEQ ID NO 1
<211> LENGTH: 917
<212> TYPE: DNA
<213> ORGANISM: Homo sapiens
<220> FEATURE:
<221> NAME/KEY: CDS
<222> LOCATION: (1)...(621)

<400> SEQUENCE: 1

| | | | | | | | | | | | | | | | | |
|---|---|---|---|---|---|---|---|---|---|---|---|---|---|---|---|---|
| atg | tat | tca | gcg | ccc | tcc | gcc | tgc | act | tgc | ctg | tgt | tta | cac | ttc | ctg | 48 |
| Met | Tyr | Ser | Ala | Pro | Ser | Ala | Cys | Thr | Cys | Leu | Cys | Leu | His | Phe | Leu | |
| 1 | | | | 5 | | | | | 10 | | | | | 15 | | |
| ctg | ctg | tgc | ttc | cag | gta | cag | gtg | ctg | gtt | gcc | gag | gag | aac | gtg | gac | 96 |
| Leu | Leu | Cys | Phe | Gln | Val | Gln | Val | Leu | Val | Ala | Glu | Glu | Asn | Val | Asp | |
| | | | 20 | | | | | 25 | | | | | 30 | | | |
| ttc | cgc | atc | cac | gtg | gag | aac | cag | acg | cgg | gct | cgg | gac | gat | gtg | agc | 144 |
| Phe | Arg | Ile | His | Val | Glu | Asn | Gln | Thr | Arg | Ala | Arg | Asp | Asp | Val | Ser | |
| | 35 | | | | | 40 | | | | | 45 | | | | | |
| cgt | aag | cag | ctg | cgg | ctg | tac | cag | ctc | tac | agc | cgg | acc | agt | ggg | aaa | 192 |
| Arg | Lys | Gln | Leu | Arg | Leu | Tyr | Gln | Leu | Tyr | Ser | Arg | Thr | Ser | Gly | Lys | |
| 50 | | | | | 55 | | | | | 60 | | | | | | |
| cac | atc | cag | gtc | ctg | ggc | cgc | agg | atc | agt | gcc | cgc | ggc | gag | gat | ggg | 240 |
| His | Ile | Gln | Val | Leu | Gly | Arg | Arg | Ile | Ser | Ala | Arg | Gly | Glu | Asp | Gly | |
| 65 | | | | 70 | | | | | 75 | | | | | 80 | | |
| gac | aag | tat | gcc | cag | ctc | cta | gtg | gag | aca | gac | acc | ttc | ggt | agt | caa | 288 |
| Asp | Lys | Tyr | Ala | Gln | Leu | Leu | Val | Glu | Thr | Asp | Thr | Phe | Gly | Ser | Gln | |
| | | | | 85 | | | | | 90 | | | | | 95 | | |
| gtc | cgg | atc | aag | ggc | aag | gag | acg | gaa | ttc | tac | ctg | tgc | atg | aac | cgc | 336 |
| Val | Arg | Ile | Lys | Gly | Lys | Glu | Thr | Glu | Phe | Tyr | Leu | Cys | Met | Asn | Arg | |
| | | | 100 | | | | | 105 | | | | | 110 | | | |
| aaa | ggc | aag | ctc | gtg | ggg | aag | ccc | gat | ggc | acc | agc | aag | gag | tgt | gtg | 384 |
| Lys | Gly | Lys | Leu | Val | Gly | Lys | Pro | Asp | Gly | Thr | Ser | Lys | Glu | Cys | Val | |
| | | 115 | | | | | 120 | | | | | 125 | | | | |
| ttc | atc | gag | aag | gtt | ctg | gag | aac | aac | tac | acg | gcc | ctg | atg | tcg | gct | 432 |
| Phe | Ile | Glu | Lys | Val | Leu | Glu | Asn | Asn | Tyr | Thr | Ala | Leu | Met | Ser | Ala | |
| | 130 | | | | | 135 | | | | | 140 | | | | | |
| aag | tac | tcc | ggc | tgg | tac | gtg | ggc | ttc | acc | aag | aag | ggg | cgg | ccg | cgg | 480 |
| Lys | Tyr | Ser | Gly | Trp | Tyr | Val | Gly | Phe | Thr | Lys | Lys | Gly | Arg | Pro | Arg | |
| 145 | | | | | 150 | | | | | 155 | | | | | 160 | |
| aag | ggc | ccc | aag | acc | cgg | gag | aac | cag | cag | gac | gtg | cat | ttc | atg | aag | 528 |
| Lys | Gly | Pro | Lys | Thr | Arg | Glu | Asn | Gln | Gln | Asp | Val | His | Phe | Met | Lys | |
| | | | | 165 | | | | | 170 | | | | | 175 | | |
| cgc | tac | ccc | aag | ggg | cag | ccg | gag | ctt | cag | aag | ccc | ttc | aag | tac | acg | 576 |
| Arg | Tyr | Pro | Lys | Gly | Gln | Pro | Glu | Leu | Gln | Lys | Pro | Phe | Lys | Tyr | Thr | |
| | | | 180 | | | | | 185 | | | | | 190 | | | |
| acg | gtg | acc | aag | agg | tcc | cgt | cgg | atc | cgg | ccc | aca | cac | cct | gcc | | 621 |
| Thr | Val | Thr | Lys | Arg | Ser | Arg | Arg | Ile | Arg | Pro | Thr | His | Pro | Ala | | |
| | 195 | | | | | 200 | | | | | 205 | | | | | | taggccaccc cgccgcggcc ctcaggtcgc cctggccaca ctcacactcc cagaaaactg      681 catcagagga atattttac atgaaaaata aggattttat tgttgacttg aaaccccga        741 tgacaaaaga ctcacgcaaa gggactgtag tcaaccccaca ggtgcttgtc tctctctagg    801 aacagacaac tctaaactcg tccccagagg aggacttgaa tgaggaaacc aacactttga    861 gaaaccaaag tccttttcc caaggttct gaaaaaaaa aaaaaaaaa ctcgag            917

<210> SEQ ID NO 2

```
<211> LENGTH: 207
<212> TYPE: PRT
<213> ORGANISM: Homo sapiens

<400> SEQUENCE: 2

Met Tyr Ser Ala Pro Ser Ala Cys Thr Cys Leu Cys Leu His Phe Leu
 1               5                  10                  15

Leu Leu Cys Phe Gln Val Gln Val Leu Val Ala Glu Glu Asn Val Asp
             20                  25                  30

Phe Arg Ile His Val Glu Asn Gln Thr Arg Ala Arg Asp Asp Val Ser
         35                  40                  45

Arg Lys Gln Leu Arg Leu Tyr Gln Leu Tyr Ser Arg Thr Ser Gly Lys
     50                  55                  60

His Ile Gln Val Leu Gly Arg Arg Ile Ser Ala Arg Gly Glu Asp Gly
 65                  70                  75                  80

Asp Lys Tyr Ala Gln Leu Leu Val Glu Thr Asp Thr Phe Gly Ser Gln
                 85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
        195                 200                 205

<210> SEQ ID NO 3
<211> LENGTH: 24
<212> TYPE: DNA
<213> ORGANISM: Artificial Sequence
<220> FEATURE:
<223> OTHER INFORMATION: oligonucleotide primer ZC11676

<400> SEQUENCE: 3
ggacttgact accgaaggtg tctg                                          24

<210> SEQ ID NO 4
<211> LENGTH: 23
<212> TYPE: DNA
<213> ORGANISM: Artificial Sequence
<220> FEATURE:
<223> OTHER INFORMATION: oligonucleotide primer ZC11677

<400> SEQUENCE: 4
gtcgatgtga gccgtaagca gct                                           23

<210> SEQ ID NO 5
<211> LENGTH: 26
<212> TYPE: DNA
<213> ORGANISM: Artificial Sequence
<220> FEATURE:
<223> OTHER INFORMATION: oligonucleotide primer ZC12053

<400> SEQUENCE: 5
```

```
-continued gcatacttgt ccccatcctc gccgcg                                          26

<210> SEQ ID NO 6
<211> LENGTH: 621
<212> TYPE: DNA
<213> ORGANISM: Artificial Sequence
<220> FEATURE:
<223> OTHER INFORMATION: degenerate sequence
<220> FEATURE:
<221> NAME/KEY: variation
<222> LOCATION: (1)...(621)
<223> OTHER INFORMATION: n is any nucleotide

<400> SEQUENCE: 6
atgtaywsng cnccnwsngc ntgyacntgy ytntgyytnc ayttyytnyt nytntgytty      60
cargtncarg tnytngtngc ngargaraay gtngayttym gnathgaygt ngaraarcar     120
acnmgngcnm gngaygaygt nwsnmgnaar carytnmgny tntaycaryt ntaywsnmgn     180
acnwsnggna arcayathca rgtnytnggn mgnmgnathw sngcnmgngg ngargayggn     240
gayaartayg cncarytnyt ngtngaracn gayacnttyg gnwsncargt nmgnathaar     300
ggnaargara cngarttyta yytntgyatg aaymgnaarg gnaarytngt nggnaarccn     360
gayggnacnw snaargartg ygtnttyath garaargtny tngaraayaa ytayacngcn     420
ytnatgwsng cnaartayws nggntggtay gtnggnttya cnaaraargg nmgnccnmgn     480
aarggnccna aracnmgnga raaycarcar gaygtncayt tyatgaarmg ntayccnaar     540
ggncarccng arytncaraa rccnttyaar tayacnacng tnacnaarmg nwsnmgnmgn     600
athmgnccna cncayccngc n                                              621

<210> SEQ ID NO 7
<211> LENGTH: 47
<212> TYPE: DNA
<213> ORGANISM: Artificial Sequence
<220> FEATURE:
<223> OTHER INFORMATION: oligonucleotide primer ZC12652

<400> SEQUENCE: 7
tatttatcta gactggttcc gcgtgccgcc gaggagaacg tggactt                   47

<210> SEQ ID NO 8
<211> LENGTH: 33
<212> TYPE: DNA
<213> ORGANISM: Artificial Sequence
<220> FEATURE:
<223> OTHER INFORMATION: oligonucleotide primer ZC12631

<400> SEQUENCE: 8
gtatttgtcg actcaggcag ggtgtgtggg ccg                                  33

<210> SEQ ID NO 9
<211> LENGTH: 22
<212> TYPE: DNA
<213> ORGANISM: Artificial Sequence
<220> FEATURE:
<223> OTHER INFORMATION: oligonucleotide primer ZC15290

<400> SEQUENCE: 9
gccgaggaga acgtggactt cc                                              22

<210> SEQ ID NO 10
<211> LENGTH: 47
<212> TYPE: DNA
<213> ORGANISM: Artificial Sequence
```

```
<220> FEATURE:
<223> OTHER INFORMATION: oligonucleotide primer ZC15270

<400> SEQUENCE: 10
tatttatcta gagatgacga tgacaaggcc gaggagaacg tggactt           47

<210> SEQ ID NO 11
<211> LENGTH: 41
<212> TYPE: DNA
<213> ORGANISM: Artificial Sequence
<220> FEATURE:
<223> OTHER INFORMATION: oligonucleotide primer ZC13497

<400> SEQUENCE: 11
agcattgcta aagaagaagg tgtaagcttg gacaagagag a                 41

<210> SEQ ID NO 12
<211> LENGTH: 63
<212> TYPE: DNA
<213> ORGANISM: Artificial Sequence
<220> FEATURE:
<223> OTHER INFORMATION: oligonucleotide primer ZC15131

<400> SEQUENCE: 12
ggtgtaagct tggacaagag agaggagaac gtggacttcc gcatccacgt ggagaaccag    60
acg                                                                  63

<210> SEQ ID NO 13
<211> LENGTH: 39
<212> TYPE: DNA
<213> ORGANISM: Artificial Sequence
<220> FEATURE:
<223> OTHER INFORMATION: oligonucleotide primer ZC15134

<400> SEQUENCE: 13
ccggctgtag agctggtaca gccgcagctg cttacggct                    39

<210> SEQ ID NO 14
<211> LENGTH: 42
<212> TYPE: DNA
<213> ORGANISM: Artificial Sequence
<220> FEATURE:
<223> OTHER INFORMATION: oligonucleotide primer ZC13529

<400> SEQUENCE: 14
cttcagaagc ccttcaagta cacgacggtg accaagaggt cc                42

<210> SEQ ID NO 15
<211> LENGTH: 61
<212> TYPE: DNA
<213> ORGANISM: Artificial Sequence
<220> FEATURE:
<223> OTHER INFORMATION: oligonucleotide primer ZC13525

<400> SEQUENCE: 15
acgacggtga ccaagaggtc ccgtcggatc cggcccacac accctgccta gggggaattc    60
g                                                                    61

<210> SEQ ID NO 16
<211> LENGTH: 61
<212> TYPE: DNA
<213> ORGANISM: Artificial Sequence
<220> FEATURE:
<223> OTHER INFORMATION: oligonucleotide primer ZC13526
```

-continued

```
<400> SEQUENCE: 16
caaacaggca gccctagaat actagtgtcg actcgaggat ccgaattccc cctaggcagg      60
g                                                                      61

<210> SEQ ID NO 17
<211> LENGTH: 44
<212> TYPE: DNA
<213> ORGANISM: Artificial Sequence
<220> FEATURE:
<223> OTHER INFORMATION: oligonucleotide primer ZC13528

<400> SEQUENCE: 17
ctcaaaaatt ataaaaatat ccaaacaggc agccctagaa tact                       44

<210> SEQ ID NO 18
<211> LENGTH: 186
<212> TYPE: DNA
<213> ORGANISM: Artificial Sequence
<220> FEATURE:
<223> OTHER INFORMATION: oligonucleotide primer ZC15132

<400> SEQUENCE: 18
gtaccgcgag cagttcccgt caatccctcc ccccttacac aggatgtcca tattaggaca      60
tctgcgtctc gaggccaccg tggttgagcc cgacactcat tcataaaacg cttgttataa    120
aagcagtggc tgcggcgcct cgtactccaa ccgcatctgc agcgagcaac tgagaagcca    180
aggatc                                                                186

<210> SEQ ID NO 19
<211> LENGTH: 141
<212> TYPE: DNA
<213> ORGANISM: Artificial Sequence
<220> FEATURE:
<223> OTHER INFORMATION: 5' linker sequence

<400> SEQUENCE: 19
agcattgctg ctaaagaaga aggtgtaagc ttggacaaga gagaggagaa cgtggacttc      60
cgcatccacg tggagaacca gacgcgggct cgggacgatg tgagccgtaa gcagctgcgg    120
ctgtaccagc tctacagccg g                                                141

<210> SEQ ID NO 20
<211> LENGTH: 144
<212> TYPE: DNA
<213> ORGANISM: Artificial Sequence
<220> FEATURE:
<223> OTHER INFORMATION: 3' linker sequence

<400> SEQUENCE: 20
cttcagaagc ccttcaagta cacgacggtg accaagaggt cccgtcggat ccggcccaca      60
caccctgcct agggggaatt cggatcctcg agtcgacact agtattctag ggctgcctgt    120
ttggatattt ttataatttt tgag                                             144

<210> SEQ ID NO 21
<211> LENGTH: 243
<212> TYPE: PRT
<213> ORGANISM: Homo sapiens

<400> SEQUENCE: 21

Met Ala Ala Ala Ile Ala Ser Ser Leu Ile Arg Gln Lys Arg Gln Ala
  1               5                  10                  15
```

```
Arg Glu Ser Asn Ser Asp Arg Val Ser Ala Ser Lys Arg Arg Ser Ser
             20                  25                  30

Pro Ser Lys Asp Gly Arg Ser Leu Cys Glu Arg His Val Leu Gly Val
         35                  40                  45

Phe Ser Lys Val Arg Phe Cys Ser Gly Arg Lys Arg Pro Val Arg Arg
 50                  55                  60

Arg Pro Glu Pro Gln Leu Lys Gly Ile Val Thr Arg Leu Phe Ser Gln
 65                  70                  75                  80

Gln Gly Tyr Phe Leu Gln Met His Pro Asp Gly Thr Ile Asp Gly Thr
                 85                  90                  95

Lys Asp Glu Asn Ser Asp Tyr Thr Leu Phe Asn Leu Ile Pro Val Gly
            100                 105                 110

Leu Arg Val Val Ala Ile Gln Gly Val Lys Ala Ser Leu Tyr Val Ala
        115                 120                 125

Met Asn Gly Glu Gly Tyr Leu Tyr Ser Ser Asp Val Phe Thr Pro Glu
    130                 135                 140

Cys Lys Phe Lys Glu Ser Val Phe Glu Asn Tyr Tyr Val Ile Tyr Ser
145                 150                 155                 160

Ser Thr Leu Tyr Arg Gln Gln Glu Ser Gly Arg Ala Trp Phe Leu Gly
                165                 170                 175

Leu Asn Lys Glu Gly Gln Ile Met Lys Gly Asn Arg Val Lys Lys Thr
            180                 185                 190

Lys Pro Ser Ser His Phe Val Pro Lys Pro Ile Glu Val Cys Met Tyr
        195                 200                 205

Arg Glu Pro Ser Leu His Glu Ile Gly Glu Lys Gln Gly Arg Ser Arg
    210                 215                 220

Lys Ser Ser Gly Thr Pro Thr Met Asn Gly Gly Lys Val Val Asn Gln
225                 230                 235                 240

Asp Ser Thr

<210> SEQ ID NO 22
<211> LENGTH: 168
<212> TYPE: PRT
<213> ORGANISM: Homo sapiens

<400> SEQUENCE: 22

Met Ala Ser Lys Glu Pro Gln Leu Lys Gly Ile Val Thr Arg Leu Phe
 1               5                  10                  15

Ser Gln Gln Gly Tyr Phe Leu Gln Met His Pro Asp Gly Thr Ile Asp
             20                  25                  30

Gly Thr Lys Asp Glu Asn Ser Asp Tyr Thr Leu Phe Asn Leu Ile Pro
         35                  40                  45

Val Gly Leu Arg Val Val Ala Ile Gln Gly Val Lys Ala Ser Leu Tyr
 50                  55                  60

Val Ala Met Asn Gly Glu Gly Tyr Leu Tyr Ser Ser Asp Val Phe Thr
 65                  70                  75                  80

Pro Glu Cys Lys Phe Lys Glu Ser Val Phe Glu Asn Tyr Tyr Val Ile
                 85                  90                  95

Tyr Ser Ser Thr Leu Tyr Arg Gln Gln Glu Ser Gly Arg Ala Trp Phe
            100                 105                 110

Leu Gly Leu Asn Lys Glu Gly Gln Ile Met Lys Gly Asn Arg Val Glu
        115                 120                 125

Lys Thr Lys Pro Ser Ser His Phe Val Pro Lys Pro Ile Glu Val Cys
    130                 135                 140
```

-continued

```
Met Tyr Arg Glu Pro Ser Leu His Glu Ile Gly Glu Asn Lys Gly Val
145                 150                 155                 160

Gln Gly Lys Phe Trp Thr Pro Pro
                165
```

<210> SEQ ID NO 23
<211> LENGTH: 247
<212> TYPE: PRT
<213> ORGANISM: Homo sapiens

<400> SEQUENCE: 23

```
Met Ala Ala Ile Ala Ser Gly Leu Ile Arg Gln Lys Arg Gln Ala
1               5                   10                  15

Arg Glu Gln His Trp Asp Arg Pro Ser Ala Ser Arg Arg Ser Ser
                20                  25                  30

Pro Ser Lys Asn Arg Gly Leu Cys Asn Gly Asn Leu Val Asp Ile Phe
                35                  40                  45

Ser Lys Val Arg Ile Phe Gly Leu Lys Lys Arg Arg Leu Arg Arg Gln
50                  55                  60

Asp Pro Gln Leu Lys Gly Ile Val Thr Arg Leu Tyr Cys Arg Gln Gly
65                  70                  75                  80

Tyr Tyr Leu Gln Met His Pro Asp Gly Ala Leu Asp Gly Thr Lys Asp
                85                  90                  95

Asp Ser Thr Asn Ser Thr Leu Phe Asn Leu Ile Pro Val Gly Leu Arg
                100                 105                 110

Val Val Ala Ile Gln Gly Val Lys Thr Gly Leu Tyr Ile Ala Met Asn
                115                 120                 125

Gly Glu Gly Tyr Leu Tyr Pro Ser Glu Leu Phe Thr Pro Glu Cys Lys
130                 135                 140

Phe Lys Glu Ser Val Phe Glu Asn Tyr Tyr Val Ile Tyr Ser Ser Met
145                 150                 155                 160

Leu Tyr Arg Gln Gln Glu Ser Gly Arg Ala Trp Phe Leu Gly Leu Asn
                165                 170                 175

Lys Glu Gly Gln Ala Met Lys Gly Asn Arg Val Lys Lys Thr Lys Pro
                180                 185                 190

Ala Ala His Phe Leu Pro Lys Pro Leu Glu Val Ala Met Tyr Arg Glu
                195                 200                 205

Pro Ser Leu His Asp Val Gly Glu Thr Val Pro Lys Pro Gly Val Thr
                210                 215                 220

Pro Ser Lys Ser Thr Ser Ala Ser Ala Ile Met Asn Gly Gly Lys Pro
225                 230                 235                 240

Val Asn Lys Ser Lys Thr Thr
                245
```

<210> SEQ ID NO 24
<211> LENGTH: 245
<212> TYPE: PRT
<213> ORGANISM: Homo sapiens

<400> SEQUENCE: 24

```
Met Ala Ala Ile Ala Ser Ser Leu Ile Arg Gln Lys Arg Gln Ala
1               5                   10                  15

Arg Glu Arg Glu Lys Ser Asn Ala Cys Lys Cys Val Ser Ser Pro Ser
                20                  25                  30

Lys Gly Lys Thr Ser Cys Asp Lys Asn Lys Leu Asn Val Phe Ser Arg
                35                  40                  45
```

```
Val Lys Leu Phe Gly Ser Lys Arg Arg Arg Arg Pro Glu Pro
 50              55              60

Gln Leu Lys Gly Ile Val Thr Lys Leu Tyr Ser Arg Gln Gly Tyr His
 65                  70                  75                  80

Leu Gln Leu Gln Ala Asp Gly Thr Ile Asp Gly Thr Lys Asp Glu Asp
                 85                  90                  95

Ser Thr Tyr Thr Leu Phe Asn Leu Ile Pro Val Gly Leu Arg Val Val
            100                 105                 110

Ala Ile Gln Gly Val Gln Thr Lys Leu Tyr Leu Ala Met Asn Ser Glu
        115                 120                 125

Gly Tyr Leu Tyr Thr Ser Glu Leu Phe Thr Pro Glu Cys Lys Phe Lys
130                 135                 140

Glu Ser Val Phe Glu Asn Tyr Tyr Val Thr Tyr Ser Ser Met Ile Tyr
145                 150                 155                 160

Arg Gln Gln Gln Ser Gly Arg Gly Trp Tyr Leu Gly Leu Asn Lys Glu
                165                 170                 175

Gly Glu Ile Met Lys Gly Asn His Val Lys Lys Asn Lys Pro Ala Ala
            180                 185                 190

His Phe Leu Pro Lys Pro Leu Lys Val Ala Met Tyr Lys Glu Pro Ser
        195                 200                 205

Leu His Asp Leu Thr Glu Phe Ser Arg Ser Gly Ser Gly Thr Pro Thr
    210                 215                 220

Lys Ser Arg Ser Val Ser Gly Val Leu Asn Gly Gly Lys Ser Met Ser
225                 230                 235                 240

His Asn Glu Ser Thr
                245

<210> SEQ ID NO 25
<211> LENGTH: 225
<212> TYPE: PRT
<213> ORGANISM: Homo sapiens

<400> SEQUENCE: 25

Met Ala Ala Leu Ala Ser Ser Leu Ile Arg Gln Lys Arg Glu Val Arg
 1               5                  10                  15

Glu Pro Gly Gly Ser Arg Pro Val Ser Ala Gln Arg Arg Val Cys Pro
                20                  25                  30

Arg Gly Thr Lys Ser Leu Cys Gln Lys Gln Leu Leu Ile Leu Leu Ser
             35                  40                  45

Lys Val Arg Leu Cys Gly Gly Arg Pro Ala Arg Pro Asp Arg Gly Pro
 50                  55                  60

Glu Pro Gln Leu Lys Gly Ile Val Thr Lys Leu Phe Cys Arg Gln Gly
 65                  70                  75                  80

Phe Tyr Leu Gln Ala Asn Pro Asp Gly Ser Ile Gln Gly Thr Pro Glu
                 85                  90                  95

Asp Thr Ser Ser Phe Thr His Phe Asn Leu Ile Pro Val Gly Leu Arg
            100                 105                 110

Val Val Thr Ile Gln Ser Ala Lys Leu Gly His Tyr Met Ala Met Asn
        115                 120                 125

Ala Glu Gly Leu Leu Tyr Ser Ser Pro His Phe Thr Ala Glu Cys Arg
130                 135                 140

Phe Lys Glu Cys Val Phe Glu Asn Tyr Tyr Val Leu Tyr Ala Ser Ala
145                 150                 155                 160

Leu Tyr Arg Gln Arg Arg Ser Gly Arg Ala Trp Tyr Leu Gly Leu Asp
                165                 170                 175
```

```
Lys Glu Gly Gln Val Met Lys Gly Asn Arg Val Lys Lys Thr Lys Ala
            180                 185                 190
Ala Ala His Phe Leu Pro Lys Leu Leu Glu Val Ala Met Tyr Gln Glu
        195                 200                 205
Pro Ser Leu His Ser Val Pro Glu Ala Ser Pro Ser Pro Pro Ala
        210                 215                 220
Pro
225

<210> SEQ ID NO 26
<211> LENGTH: 206
<212> TYPE: PRT
<213> ORGANISM: Homo sapiens

<400> SEQUENCE: 26

Met Ser Gly Pro Gly Thr Ala Ala Val Ala Leu Leu Pro Ala Val Leu
 1               5                  10                  15
Leu Ala Leu Leu Ala Pro Trp Ala Gly Arg Gly Gly Ala Ala Ala Pro
            20                  25                  30
Thr Ala Pro Asn Gly Thr Leu Glu Ala Glu Leu Glu Arg Arg Trp Glu
        35                  40                  45
Ser Leu Val Ala Leu Ser Leu Ala Arg Leu Pro Val Ala Ala Gln Pro
    50                  55                  60
Lys Glu Ala Ala Val Gln Ser Gly Ala Gly Asp Tyr Leu Leu Gly Ile
65                  70                  75                  80
Lys Arg Leu Arg Arg Leu Tyr Cys Asn Val Gly Ile Gly Phe His Leu
                85                  90                  95
Gln Ala Leu Pro Asp Gly Arg Ile Gly Gly Ala His Ala Asp Thr Arg
            100                 105                 110
Asp Ser Leu Leu Glu Leu Ser Pro Val Glu Arg Gly Val Val Ser Ile
        115                 120                 125
Phe Gly Val Ala Ser Arg Phe Phe Val Ala Met Ser Ser Lys Gly Lys
    130                 135                 140
Leu Tyr Gly Ser Pro Phe Phe Thr Asp Glu Cys Thr Phe Lys Glu Ile
145                 150                 155                 160
Leu Leu Pro Asn Asn Tyr Asn Ala Tyr Glu Ser Tyr Lys Tyr Pro Gly
                165                 170                 175
Met Phe Ile Ala Leu Ser Lys Asn Gly Lys Thr Lys Lys Gly Asn Arg
            180                 185                 190
Val Ser Pro Thr Met Lys Val Thr His Phe Leu Pro Arg Leu
        195                 200                 205

<210> SEQ ID NO 27
<211> LENGTH: 208
<212> TYPE: PRT
<213> ORGANISM: Homo sapiens

<400> SEQUENCE: 27

Met Ala Leu Gly Gln Lys Leu Phe Ile Thr Met Ser Arg Gly Ala Gly
 1               5                  10                  15
Arg Leu Gln Gly Thr Leu Trp Ala Leu Val Phe Leu Gly Ile Leu Val
            20                  25                  30
Gly Met Val Val Pro Ser Pro Ala Gly Thr Arg Ala Asn Asn Thr Leu
        35                  40                  45
Leu Asp Ser Arg Gly Trp Gly Thr Leu Leu Ser Arg Ser Arg Ala Gly
    50                  55                  60
```

```
Leu Ala Gly Glu Ile Ala Gly Val Asn Trp Glu Ser Gly Tyr Leu Val
 65                  70                  75                  80

Gly Ile Lys Arg Gln Arg Arg Leu Tyr Cys Asn Val Gly Ile Gly Phe
                 85                  90                  95

His Leu Gln Val Leu Pro Asp Gly Arg Ile Ser Gly Thr His Glu Glu
            100                 105                 110

Asn Pro Tyr Ser Leu Leu Glu Ile Ser Thr Val Glu Arg Gly Val Val
        115                 120                 125

Ser Leu Phe Gly Val Arg Ser Ala Leu Phe Val Ala Met Asn Ser Lys
    130                 135                 140

Gly Arg Leu Tyr Ala Thr Pro Ser Phe Gln Glu Glu Cys Lys Phe Arg
145                 150                 155                 160

Glu Thr Leu Leu Pro Asn Asn Tyr Asn Ala Tyr Glu Ser Asp Leu Tyr
                165                 170                 175

Gln Gly Thr Tyr Ile Ala Leu Ser Lys Tyr Gly Arg Val Lys Arg Gly
            180                 185                 190

Ser Lys Val Ser Pro Ile Met Thr Val Thr His Phe Leu Pro Arg Ile
        195                 200                 205

<210> SEQ ID NO 28
<211> LENGTH: 155
<212> TYPE: PRT
<213> ORGANISM: Homo sapiens

<400> SEQUENCE: 28

Met Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Lys Arg Leu
                20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
        50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 29
<211> LENGTH: 155
<212> TYPE: PRT
<213> ORGANISM: Homo sapiens

<400> SEQUENCE: 29

Met Ala Glu Gly Glu Ile Thr Thr Phe Thr Ala Leu Thr Glu Lys Phe
 1               5                  10                  15

Asn Leu Pro Pro Gly Asn Tyr Lys Lys Pro Lys Leu Leu Tyr Cys Ser
                20                  25                  30
```

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
 50                  55                  60

Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
                115                 120                 125

Asn Gly Ser Cys Lys Arg Gly Pro Arg Thr His Tyr Gly Gln Lys Ala
                130                 135                 140

Ile Leu Phe Leu Pro Leu Pro Val Ser Ser Asp
 145                 150                 155

<210> SEQ ID NO 30
<211> LENGTH: 208
<212> TYPE: PRT
<213> ORGANISM: Homo sapiens

<400> SEQUENCE: 30

Met Trp Lys Trp Ile Leu Thr His Cys Ala Ser Ala Phe Pro His Leu
  1               5                  10                  15

Pro Gly Cys Cys Cys Cys Cys Phe Leu Leu Phe Leu Val Ser Ser
                20                  25                  30

Val Pro Val Thr Cys Gln Ala Leu Gly Gln Asp Met Val Ser Pro Glu
                35                  40                  45

Ala Thr Asn Ser Ser Ser Ser Phe Ser Ser Pro Ser Ser Ala Gly
                50                  55                  60

Arg His Val Arg Ser Tyr Asn His Leu Gln Gly Asp Val Arg Trp Arg
 65                  70                  75                  80

Lys Leu Phe Ser Phe Thr Lys Tyr Phe Leu Lys Ile Glu Lys Asn Gly
                85                  90                  95

Lys Val Ser Gly Thr Lys Lys Glu Asn Cys Pro Tyr Ser Ile Leu Glu
                100                 105                 110

Ile Thr Ser Val Glu Ile Gly Val Val Ala Val Lys Ala Ile Asn Ser
                115                 120                 125

Asn Tyr Tyr Leu Ala Met Asn Lys Lys Gly Lys Leu Tyr Gly Ser Lys
                130                 135                 140

Glu Phe Asn Asn Asp Cys Lys Leu Lys Glu Arg Ile Glu Glu Asn Gly
 145                 150                 155                 160

Tyr Asn Thr Tyr Ala Ser Phe Asn Trp Gln His Asn Gly Arg Gln Met
                165                 170                 175

Tyr Val Ala Leu Asn Gly Lys Gly Ala Pro Arg Arg Gly Gln Lys Thr
                180                 185                 190

Arg Arg Lys Asn Thr Ser Ala His Phe Leu Pro Met Val Val His Ser
                195                 200                 205

<210> SEQ ID NO 31
<211> LENGTH: 194
<212> TYPE: PRT
<213> ORGANISM: Homo sapiens

<400> SEQUENCE: 31

-continued

```
Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
            20                  25                  30

Asn Asp Met Thr Pro Glu Gln Met Ala Thr Asn Val Asn Cys Ser Ser
        35                  40                  45

Pro Glu Arg His Thr Arg Ser Tyr Asp Tyr Met Glu Gly Gly Asp Ile
    50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
            100                 105                 110

Val Glu Ser Glu Phe Tyr Leu Ala Met Asn Lys Glu Gly Lys Leu Tyr
            115                 120                 125

Ala Lys Lys Glu Cys Asn Glu Asp Cys Asn Phe Lys Glu Leu Ile Leu
        130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
                180                 185                 190

Ile Thr

<210> SEQ ID NO 32
<211> LENGTH: 233
<212> TYPE: PRT
<213> ORGANISM: Homo sapiens

<400> SEQUENCE: 32

Met Gly Ser Pro Arg Ser Ala Leu Ser Cys Leu Leu His Leu Leu
1               5                   10                  15

Val Leu Cys Leu Gln Ala Gln Glu Gly Pro Gly Arg Gly Pro Ala Leu
            20                  25                  30

Gly Arg Glu Leu Ala Ser Leu Phe Arg Ala Gly Arg Glu Pro Gln Gly
        35                  40                  45

Val Ser Gln Gln His Val Arg Glu Gln Ser Leu Val Thr Asp Gln Leu
    50                  55                  60

Ser Arg Arg Leu Ile Arg Thr Tyr Gln Leu Tyr Ser Arg Thr Ser Gly
65                  70                  75                  80

Lys His Val Gln Val Leu Ala Asn Lys Arg Ile Asn Ala Met Ala Glu
                85                  90                  95

Asp Gly Asp Pro Phe Ala Lys Leu Ile Val Glu Thr Asp Thr Phe Gly
            100                 105                 110

Ser Arg Val Arg Val Arg Gly Ala Glu Thr Gly Leu Tyr Ile Cys Met
            115                 120                 125

Asn Lys Lys Gly Lys Leu Ile Ala Lys Ser Asn Gly Lys Gly Lys Asp
        130                 135                 140

Cys Val Phe Thr Glu Ile Val Leu Glu Asn Asn Tyr Thr Ala Leu Gln
145                 150                 155                 160

Asn Ala Lys Tyr Glu Gly Trp Tyr Met Ala Phe Thr Arg Lys Gly Arg
                165                 170                 175
```

```
Pro Arg Lys Gly Ser Lys Thr Arg Gln His Gln Arg Glu Val His Phe
            180                 185                 190

Met Lys Arg Leu Pro Arg Gly His His Thr Thr Glu Gln Ser Leu Arg
            195                 200                 205

Phe Glu Phe Leu Asn Tyr Pro Pro Phe Thr Arg Ser Leu Arg Gly Ser
            210                 215                 220

Gln Arg Thr Trp Ala Pro Glu Pro Arg
225                 230
```

<210> SEQ ID NO 33
<211> LENGTH: 268
<212> TYPE: PRT
<213> ORGANISM: Homo sapiens

<400> SEQUENCE: 33

```
Met Ser Leu Ser Phe Leu Leu Leu Phe Ser His Leu Ile Leu
 1               5                  10                 15

Ser Ala Trp Ala His Gly Glu Lys Arg Leu Ala Pro Lys Gly Gln Pro
            20                  25                  30

Gly Pro Ala Ala Thr Asp Arg Asn Pro Ile Gly Ser Ser Arg Gln
            35                  40                  45

Ser Ser Ser Ser Ala Met Ser Ser Ser Ala Ser Ser Pro Ala
50                  55                  60

Ala Ser Leu Gly Ser Gln Gly Ser Gly Leu Glu Gln Ser Ser Phe Gln
65                  70                  75                  80

Trp Ser Pro Ser Gly Arg Arg Thr Gly Ser Leu Tyr Cys Arg Val Gly
            85                  90                  95

Ile Gly Phe His Leu Gln Ile Tyr Pro Asp Gly Lys Val Asn Gly Ser
            100                 105                 110

His Glu Ala Asn Met Leu Ser Val Leu Glu Ile Phe Ala Val Ser Gln
            115                 120                 125

Gly Ile Val Gly Ile Arg Gly Val Phe Ser Asn Lys Phe Leu Ala Met
            130                 135                 140

Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
            165                 170                 175

Ala Ile His Arg Thr Glu Lys Thr Gly Arg Glu Trp Tyr Val Ala Leu
            180                 185                 190

Asn Lys Arg Gly Lys Ala Lys Arg Gly Cys Ser Pro Arg Val Lys Pro
            195                 200                 205

Gln His Ile Ser Thr His Phe Leu Pro Arg Phe Lys Gln Ser Glu Gln
            210                 215                 220

Pro Glu Leu Ser Phe Thr Val Thr Val Pro Glu Lys Lys Asn Pro Pro
225                 230                 235                 240

Ser Pro Ile Lys Ser Lys Ile Pro Leu Ser Ala Pro Arg Lys Asn Thr
            245                 250                 255

Asn Ser Val Lys Tyr Arg Leu Lys Phe Arg Phe Gly
            260                 265
```

<210> SEQ ID NO 34
<211> LENGTH: 208
<212> TYPE: PRT
<213> ORGANISM: Homo sapiens

<400> SEQUENCE: 34

-continued

Met Ala Pro Leu Gly Glu Val Gly Asn Tyr Phe Gly Val Gln Asp Ala
1               5                  10                 15

Val Pro Phe Gly Asn Val Pro Val Leu Pro Val Asp Ser Pro Val Leu
            20                 25                 30

Leu Ser Asp His Leu Gly Gln Ser Glu Ala Gly Gly Leu Pro Arg Gly
            35                 40                 45

Pro Ala Val Thr Asp Leu Asp His Leu Lys Gly Ile Leu Arg Arg Arg
        50                 55                 60

Gln Leu Tyr Cys Arg Thr Gly Phe His Leu Glu Ile Phe Pro Asn Gly
65                  70                 75                 80

Thr Ile Gln Gly Thr Arg Lys Asp His Ser Arg Phe Gly Ile Leu Glu
            85                 90                 95

Phe Ile Ser Ile Ala Val Gly Leu Val Ser Ile Arg Gly Val Asp Ser
            100                105                110

Gly Leu Tyr Leu Gly Met Asn Glu Lys Gly Glu Leu Tyr Gly Ser Glu
            115                120                125

Lys Leu Thr Gln Glu Cys Val Phe Arg Glu Gln Phe Glu Glu Asn Trp
            130                135                140

Tyr Asn Thr Tyr Ser Ser Asn Leu Tyr Lys His Val Asp Thr Gly Arg
145                 150                155                160

Arg Tyr Tyr Val Ala Leu Asn Lys Asp Gly Thr Pro Arg Glu Gly Thr
                165                170                175

Arg Thr Lys Arg His Gln Lys Phe Thr His Phe Leu Pro Arg Pro Val
            180                185                190

Asp Pro Asp Lys Val Pro Glu Leu Tyr Lys Asp Ile Leu Ser Gln Ser
            195                200                205

<210> SEQ ID NO 35
<211> LENGTH: 239
<212> TYPE: PRT
<213> ORGANISM: Homo sapiens

<400> SEQUENCE: 35

Met Gly Leu Ile Trp Leu Leu Leu Ser Leu Leu Glu Pro Gly Trp
1               5                  10                 15

Pro Ala Ala Gly Pro Gly Ala Arg Leu Arg Arg Asp Ala Gly Gly Arg
            20                 25                 30

Gly Gly Val Tyr Glu His Leu Gly Gly Ala Pro Arg Arg Arg Lys Leu
            35                 40                 45

Tyr Cys Ala Thr Lys Tyr His Leu Gln Leu His Pro Ser Gly Arg Val
        50                 55                 60

Asn Gly Ser Leu Glu Asn Ser Ala Tyr Ser Ile Leu Glu Ile Thr Ala
65                  70                 75                 80

Val Glu Val Gly Ile Val Ala Ile Arg Gly Leu Phe Ser Gly Arg Tyr
            85                 90                 95

Leu Ala Met Asn Lys Arg Gly Arg Leu Tyr Ala Ser Glu His Tyr Ser
            100                105                110

Ala Glu Cys Glu Phe Val Glu Arg Ile His Glu Leu Gly Tyr Asn Thr
            115                120                125

Tyr Ala Ser Arg Leu Tyr Arg Thr Val Ser Ser Thr Pro Gly Ala Arg
        130                135                140

Arg Gln Pro Ser Ala Glu Arg Leu Trp Tyr Val Ser Val Asn Gly Lys
145                 150                155                160

Gly Arg Pro Arg Arg Gly Phe Lys Thr Arg Arg Thr Gln Lys Ser Ser

-continued

```
                        165                 170                 175
Leu Phe Leu Pro Arg Val Leu Asp His Arg Asp His Glu Met Val Arg
                180                 185                 190

Gln Leu Gln Ser Gly Leu Pro Arg Pro Pro Gly Lys Gly Val Gln Pro
            195                 200                 205

Arg Arg Arg Arg Gln Lys Gln Ser Pro Asp Asn Leu Glu Pro Ser His
        210                 215                 220

Val Gln Ala Ser Arg Leu Gly Ser Gln Leu Glu Ala Ser Ala His
225                 230                 235
```

<210> SEQ ID NO 36
<211> LENGTH: 11
<212> TYPE: PRT
<213> ORGANISM: Artificial Sequence
<220> FEATURE:
<223> OTHER INFORMATION: FGF family motif
<220> FEATURE:
<221> NAME/KEY: VARIANT
<222> LOCATION: (1)...(11)
<223> OTHER INFORMATION: Xaa is any amino acid

<400> SEQUENCE: 36

```
Cys Xaa Phe Xaa Glu Glu Glu Glu Glu Glu Tyr
 1               5                  10
```

<210> SEQ ID NO 37
<211> LENGTH: 4
<212> TYPE: PRT
<213> ORGANISM: Artificial Sequence
<220> FEATURE:
<223> OTHER INFORMATION: dibasic cleavage peptide
<220> FEATURE:
<221> NAME/KEY: VARIANT
<222> LOCATION: (2)...(3)
<223> OTHER INFORMATION: Xaa is any amino acid

<400> SEQUENCE: 37

```
Arg Xaa Xaa Arg
 1
```

<210> SEQ ID NO 38
<211> LENGTH: 1023
<212> TYPE: DNA
<213> ORGANISM: Mus musculus
<220> FEATURE:
<221> NAME/KEY: CDS
<222> LOCATION: (1)...(624)

<400> SEQUENCE: 38

```
atg tat tca gcg ccc tcc gcc tgc act tgc ctg tgt tta cac ttt cta      48
Met Tyr Ser Ala Pro Ser Ala Cys Thr Cys Leu Cys Leu His Phe Leu
 1               5                  10                  15 ctg ctg tgc ttc cag gtt cag gtg ttg gca gcc gag gag aat gtg gac      96
Leu Leu Cys Phe Gln Val Gln Val Leu Ala Ala Glu Glu Asn Val Asp
                20                  25                  30 ttc cgc atc cac gtg gag aac cag acg cgg gct cga gat gat gtg agt     144
Phe Arg Ile His Val Glu Asn Gln Thr Arg Ala Arg Asp Asp Val Ser
            35                  40                  45 cgg aag cag ctg cgc ttg tac cag ctc tat agc agg acc agt ggg aag     192
Arg Lys Gln Leu Arg Leu Tyr Gln Leu Tyr Ser Arg Thr Ser Gly Lys
        50                  55                  60 cac att caa gtc ctg ggc cgt agg atc agt gcc cgt ggc gag gac ggg     240
His Ile Gln Val Leu Gly Arg Arg Ile Ser Ala Arg Gly Glu Asp Gly
65                  70                  75                  80
```

-continued

```
gac aag tat gcc cag ctc cta gtg gag aca gat acc ttc ggg agt caa        288
Asp Lys Tyr Ala Gln Leu Leu Val Glu Thr Asp Thr Phe Gly Ser Gln
            85                  90                  95 gtc cgg atc aag ggc aag gag aca gaa ttc tac ctg tgt atg aac cga        336
Val Arg Ile Lys Gly Lys Glu Thr Glu Phe Tyr Leu Cys Met Asn Arg
        100                 105                 110 aaa ggc aag ctc gtg ggg aag cct gat ggt act agc aag gag tgc gtg        384
Lys Gly Lys Leu Val Gly Lys Pro Asp Gly Thr Ser Lys Glu Cys Val
            115                 120                 125 ttc att gag aag gtt ctg gaa aac aac tac acg gcc ctg atg tct gcc        432
Phe Ile Glu Lys Val Leu Glu Asn Asn Tyr Thr Ala Leu Met Ser Ala
    130                 135                 140 aag tac tct ggt tgg tat gtg ggc ttc acc aag aag ggg cgg cct cgc        480
Lys Tyr Ser Gly Trp Tyr Val Gly Phe Thr Lys Lys Gly Arg Pro Arg
145                 150                 155                 160 aag ggt ccc aag acc cgc gag aac caa caa gat gta cac ttc atg aag        528
Lys Gly Pro Lys Thr Arg Glu Asn Gln Gln Asp Val His Phe Met Lys
                165                 170                 175 cgt tac ccc aag gga cag gcc gag ctg cag aag ccc ttc aaa tac acc        576
Arg Tyr Pro Lys Gly Gln Ala Glu Leu Gln Lys Pro Phe Lys Tyr Thr
            180                 185                 190 aca gtc acc aag cga tcc cgg cgg atc cgc ccc act cac ccc ggc tag        624
Thr Val Thr Lys Arg Ser Arg Arg Ile Arg Pro Thr His Pro Gly
        195                 200                 205 gtccggccac actcaccccc ccagagaact acatcagagg aatattttta catgaaaaat      684
aaggaagaat ctctattttt gtacattgtg tttaaaagaa gacaaaaact gaacctaaag      744
tcttgggagg aggggcgata ggattccact gttgacctga accccatgac aaaggactca      804
cacaagggga ccgctgtcaa cccacaggtg cttgcctctc tctaggaggt gacaattcaa      864
aactcatccc cagaggagga cttgaacgag gaaactgcga gaaaccaaag tcctttcccc      924
ccaaaggttc tgaaagcaaa caaaaaaaaa aaaaaaaaaa aaaaaaaaaa aaaaaaaaa       984 aaaaaaaaaa aaaaaaaaaa gggcggccgc tctagagga                            1023
```

<210> SEQ ID NO 39
<211> LENGTH: 207
<212> TYPE: PRT
<213> ORGANISM: Mus musculus

<400> SEQUENCE: 39

```
Met Tyr Ser Ala Pro Ser Ala Cys Thr Cys Leu Cys Leu His Phe Leu
1               5                   10                  15

Leu Leu Cys Phe Gln Val Gln Val Leu Ala Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
            85                  90                  95

Val Arg Ile Lys Gly Lys Glu Thr Glu Phe Tyr Leu Cys Met Asn Arg
        100                 105                 110

Lys Gly Lys Leu Val Gly Lys Pro Asp Gly Thr Ser Lys Glu Cys Val
    115                 120                 125

Phe Ile Glu Lys Val Leu Glu Asn Asn Tyr Thr Ala Leu Met Ser Ala
```

-continued

```
                130               135               140
Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Ala Glu Leu Gln Lys Pro Phe Lys Tyr Thr
            180                 185                 190

Thr Val Thr Lys Arg Ser Arg Arg Ile Arg Pro Thr His Pro Gly
        195                 200                 205

<210> SEQ ID NO 40
<211> LENGTH: 21
<212> TYPE: DNA
<213> ORGANISM: Artificial Sequence
<220> FEATURE:
<223> OTHER INFORMATION: Oligonucleotide primer: ZC17579

<400> SEQUENCE: 40
aaaggcaagc tcgtggggaa g                                          21

<210> SEQ ID NO 41
<211> LENGTH: 22
<212> TYPE: DNA
<213> ORGANISM: Artificial Sequence
<220> FEATURE:
<223> OTHER INFORMATION: Oligonucleotide primer: ZC17578

<400> SEQUENCE: 41
tcgcttggtg actgtggtgt at                                         22

<210> SEQ ID NO 42
<211> LENGTH: 19
<212> TYPE: DNA
<213> ORGANISM: Artificial Sequence
<220> FEATURE:
<223> OTHER INFORMATION: Oligonucleotide primer: ZC19567

<400> SEQUENCE: 42
atgtattcag cgccctccg                                             19

<210> SEQ ID NO 43
<211> LENGTH: 19
<212> TYPE: DNA
<213> ORGANISM: Artificial Sequence
<220> FEATURE:
<223> OTHER INFORMATION: Oligonucleotide primer: ZC19633

<400> SEQUENCE: 43
cgagcccgcg tctggttct                                             19
```